(12) United States Patent
Atalar et al.

(10) Patent No.: US 9,242,090 B2
(45) Date of Patent: Jan. 26, 2016

(54) MRI COMPATIBLE MEDICAL LEADS

(71) Applicants: MRI Interventions, Inc., Memphis, TN (US); Greatbatch Ltd., Clarence, NY (US)

(72) Inventors: Ergin Atalar, Ankara (TR); Robert Susil; Albert Lardo, Baldwin, MD (US); Henry R. Halperin, Pikesville, MD (US)

(73) Assignees: MRI Interventions Inc., Memphis, TN (US); Greatbatch Ltd., Clarence, NY (US)

( * ) Notice: Subject to any disclaimer, the term of this patent is extended or adjusted under 35 U.S.C. 154(b) by 0 days.

(21) Appl. No.: 14/326,183

(22) Filed: Jul. 8, 2014

(65) Prior Publication Data

US 2015/0031975 A1  Jan. 29, 2015

Related U.S. Application Data

(63) Continuation of application No. 11/560,055, filed on Nov. 15, 2006, now abandoned, which is a continuation of application No. 10/123,534, filed on Apr. 15, 2002, now Pat. No. 7,844,319.

(60) Provisional application No. 60/283,725, filed on Apr. 13, 2001.

(51) Int. Cl.
| *A61N 1/00* | (2006.01) |
| *A61N 1/08* | (2006.01) |
| *A61N 1/05* | (2006.01) |
| *A61B 5/042* | (2006.01) |

(Continued)

(52) U.S. Cl.
CPC . *A61N 1/08* (2013.01); *A61B 5/042* (2013.01); *A61B 18/14* (2013.01); *A61N 1/05* (2013.01); *A61N 1/056* (2013.01); *A61N 1/3718* (2013.01); *A61N 2001/086* (2013.01)

(58) Field of Classification Search
CPC ..................... A61N 2001/086; A61N 1/3718
See application file for complete search history.

(56) References Cited

U.S. PATENT DOCUMENTS

| 3,871,382 A | 3/1975 | Mann |
| 3,968,802 A | 7/1976 | Ballis |

(Continued)

FOREIGN PATENT DOCUMENTS

| EP | 0243573 A2 | 11/1987 |
| EP | 0145430 B1 | 5/1991 |

(Continued)

OTHER PUBLICATIONS

Balanis, C., "Advanced Engineering Electromagnetics," John Wiley & Sons, Inc., Chapters 1, 2, and 7 (1989).

(Continued)

*Primary Examiner* — Scott Getzow
(74) *Attorney, Agent, or Firm* — Lowe Graham Jones PLLC; Bruce E. Black

(57) ABSTRACT

Herein is disclosed a probe, including a first electrode disposed at least partially on the probe surface, a second electrode disposed at least partially on the probe surface, a first conductor electrically coupled to the first electrode, a second conductor electrically coupled to the second electrode, and a reactive element electrically coupling the first conductor and the second conductor.

14 Claims, 8 Drawing Sheets

(51) Int. Cl.
*A61B 18/14* (2006.01)
*A61N 1/37* (2006.01)

(56) References Cited

U.S. PATENT DOCUMENTS

| | | | |
|---|---|---|---|
| 4,295,467 A | 10/1981 | Mann et al. |
| 4,431,005 A | 2/1984 | McCormick |
| 4,445,501 A | 5/1984 | Bresler |
| 4,572,198 A | 2/1986 | Codrington |
| 4,633,181 A | 12/1986 | Murphy-Boesch et al. |
| 4,643,186 A | 2/1987 | Rosen et al. |
| 4,654,880 A | 3/1987 | Sontag |
| 4,672,972 A | 6/1987 | Berke |
| 4,682,125 A | 7/1987 | Harrison et al. |
| 4,689,621 A | 8/1987 | Kleinberg |
| 4,754,752 A | 7/1988 | Ginsburg et al. |
| 4,757,820 A | 7/1988 | Itoh |
| 4,766,381 A | 8/1988 | Conturo et al. |
| 4,799,499 A | 1/1989 | Bisping |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,858,623 A | 8/1989 | Bradshaw et al. |
| 4,859,950 A | 8/1989 | Keren |
| 4,932,411 A | 6/1990 | Fritschy et al. |
| 4,951,672 A | 8/1990 | Buchwald et al. |
| 4,960,106 A | 10/1990 | Kubokawa |
| 4,989,608 A | 2/1991 | Ratner |
| 5,019,075 A | 5/1991 | Spears et al. |
| 5,095,911 A | 3/1992 | Pomeranz |
| 5,099,208 A | 3/1992 | Fitzpatrick et al. |
| 5,167,233 A | 12/1992 | Eberle et al. |
| 5,170,789 A | 12/1992 | Narayan et al. |
| 5,178,618 A | 1/1993 | Kandarpa |
| 5,190,046 A | 3/1993 | Shturman |
| 5,209,233 A | 5/1993 | Holland et al. |
| 5,211,165 A | 5/1993 | Dumoulin et al. |
| 5,217,010 A | 6/1993 | Tsitlik et al. |
| 5,246,438 A | 9/1993 | Langberg |
| 5,251,120 A | 10/1993 | Smith |
| 5,271,400 A | 12/1993 | Dumoulin et al. |
| 5,300,108 A | 4/1994 | Rebell et al. |
| 5,307,808 A | 5/1994 | Dumoulin et al. |
| 5,307,814 A | 5/1994 | Kressel et al. |
| 5,315,025 A | 5/1994 | Bushell et al. |
| 5,318,025 A | 6/1994 | Dumoulin et al. |
| 5,323,776 A | 6/1994 | Blakeley et al. |
| 5,323,778 A | 6/1994 | Kandarpa et al. |
| 5,333,095 A | 7/1994 | Stevenson et al. |
| 5,334,193 A | 8/1994 | Nardella |
| 5,348,010 A | 9/1994 | Schnall et al. |
| 5,352,979 A | 10/1994 | Conturo |
| 5,355,087 A | 10/1994 | Claiborne et al. |
| 5,358,515 A | 10/1994 | Hürter et al. |
| 5,363,845 A | 11/1994 | Chowdhury et al. |
| 5,365,928 A | 11/1994 | Rhinehart et al. |
| 5,370,644 A | 12/1994 | Langberg |
| 5,398,683 A | 3/1995 | Edwards et al. |
| 5,400,787 A | 3/1995 | Marandos |
| 5,413,104 A | 5/1995 | Buijs et al. |
| 5,419,325 A | 5/1995 | Dumoulin et al. |
| 5,433,717 A | 7/1995 | Rubinsky et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,451,232 A | 9/1995 | Rhinehart et al. |
| 5,462,055 A | 10/1995 | Casey et al. |
| 5,476,095 A | 12/1995 | Schnall et al. |
| 5,498,261 A | 3/1996 | Strul |
| 5,507,743 A | 4/1996 | Edwards et al. |
| 5,512,825 A | 4/1996 | Atalar et al. |
| 5,514,173 A | 5/1996 | Rebell et al. |
| 5,531,768 A * | 7/1996 | Alferness ............ 607/6 |
| 5,540,679 A | 7/1996 | Fram et al. |
| 5,540,959 A | 7/1996 | Wang |
| 5,545,201 A | 8/1996 | Helland et al. |
| 5,558,093 A | 9/1996 | Pomeranz |
| 5,578,008 A | 11/1996 | Hara |
| 5,588,432 A | 12/1996 | Crowley |
| 5,590,657 A | 1/1997 | Cain et al. |
| 5,620,476 A | 4/1997 | Truex et al. |
| 5,623,241 A | 4/1997 | Minkoff |
| 5,629,622 A | 5/1997 | Scampini |
| 5,647,361 A | 7/1997 | Damadian |
| 5,662,108 A | 9/1997 | Budd et al. |
| 5,682,897 A | 11/1997 | Pomeranz |
| 5,685,878 A | 11/1997 | Falwell et al. |
| 5,697,958 A | 12/1997 | Paul et al. |
| 5,699,801 A | 12/1997 | Atalar et al. |
| 5,706,810 A | 1/1998 | Rubinsky et al. |
| 5,715,825 A | 2/1998 | Crowley |
| 5,716,390 A | 2/1998 | Li |
| 5,722,998 A | 3/1998 | Prutchi et al. |
| 5,741,321 A | 4/1998 | Brennen |
| 5,751,539 A | 5/1998 | Stevenson et al. |
| 5,759,202 A | 6/1998 | Schroeppel |
| 5,769,800 A | 6/1998 | Gelfand et al. |
| 5,775,338 A | 7/1998 | Hastings |
| 5,779,669 A | 7/1998 | Haissaguerre et al. |
| 5,782,891 A | 7/1998 | Hassler et al. |
| 5,792,055 A | 8/1998 | McKinnon |
| 5,827,997 A | 10/1998 | Chung et al. |
| 5,833,608 A | 11/1998 | Acker |
| 5,836,992 A | 11/1998 | Thompson et al. |
| 5,840,031 A | 11/1998 | Crowley |
| 5,864,234 A | 1/1999 | Ludeke |
| 5,868,674 A | 2/1999 | Glowinski et al. |
| 5,879,347 A | 3/1999 | Saadat |
| 5,891,134 A | 4/1999 | Goble et al. |
| 5,896,267 A | 4/1999 | Hittman et al. |
| 5,905,627 A | 5/1999 | Brendel et al. |
| 5,916,162 A | 6/1999 | Smelten et al. |
| 5,928,145 A | 7/1999 | Ocali et al. |
| 5,928,159 A | 7/1999 | Eggers et al. |
| 5,938,609 A | 8/1999 | Pomeranz |
| 5,938,692 A | 8/1999 | Rudie |
| 5,959,829 A | 9/1999 | Stevenson et al. |
| 5,964,705 A | 10/1999 | Truwit et al. |
| 5,973,906 A | 10/1999 | Stevenson et al. |
| 5,978,204 A | 11/1999 | Stevenson |
| 6,004,269 A | 12/1999 | Crowley et al. |
| 6,008,980 A | 12/1999 | Stevenson et al. |
| 6,011,995 A | 1/2000 | Guglielmi et al. |
| 6,018,683 A | 1/2000 | Verness et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,045,532 A | 4/2000 | Eggers et al. |
| 6,055,457 A | 4/2000 | Bonner |
| 6,066,136 A | 5/2000 | Geistert |
| 6,101,417 A | 8/2000 | Vogel et al. |
| 6,119,042 A | 9/2000 | Verness et al. |
| 6,128,522 A | 10/2000 | Acker et al. |
| 6,129,670 A | 10/2000 | Burdette et al. |
| 6,141,594 A | 10/2000 | Flynn et al. |
| 6,159,560 A | 12/2000 | Stevenson et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,226,545 B1 | 5/2001 | Gilderdale |
| 6,236,205 B1 | 5/2001 | Luedeke et al. |
| 6,238,390 B1 | 5/2001 | Tu et al. |
| 6,253,111 B1 * | 6/2001 | Carner ............ 607/122 |
| 6,263,229 B1 | 7/2001 | Atalar et al. |
| 6,272,370 B1 | 8/2001 | Gillies et al. |
| 6,275,369 B1 | 8/2001 | Stevenson et al. |
| 6,280,385 B1 | 8/2001 | Melzer et al. |
| 6,284,971 B1 | 9/2001 | Atalar et al. |
| 6,285,910 B1 | 9/2001 | Verness et al. |
| 6,332,089 B1 | 12/2001 | Acker et al. |
| 6,390,996 B1 | 5/2002 | Halperin et al. |
| 6,408,202 B1 | 6/2002 | Lima et al. |
| 6,414,835 B1 | 7/2002 | Wolf et al. |

(56) References Cited

U.S. PATENT DOCUMENTS

| | | |
|---|---|---|
| 6,424,234 B1 | 7/2002 | Stevenson |
| 6,428,537 B1 | 8/2002 | Swanson et al. |
| 6,456,481 B1 | 9/2002 | Stevenson |
| 6,459,935 B1 | 10/2002 | Piersma |
| 6,473,291 B1 | 10/2002 | Stevenson |
| 6,493,591 B1 | 12/2002 | Stokes |
| 6,496,006 B1 | 12/2002 | Vrijheid |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,549,800 B1 | 4/2003 | Atalar et al. |
| 6,556,009 B2 | 4/2003 | Kellman et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,593,884 B1 | 7/2003 | Gilboa et al. |
| 6,606,513 B2 | 8/2003 | Lardo et al. |
| 6,628,980 B2 | 9/2003 | Atalar et al. |
| 6,633,780 B1 | 10/2003 | Berger et al. |
| 6,643,903 B2 | 11/2003 | Stevenson et al. |
| 6,654,628 B1 | 11/2003 | Silber et al. |
| 6,675,033 B1 | 1/2004 | Lardo et al. |
| 6,675,779 B2 | 1/2004 | King et al. |
| 6,687,550 B1 | 2/2004 | Doan |
| 6,690,963 B2 | 2/2004 | Ben-Haim et al. |
| 6,701,176 B1 | 3/2004 | Halperin et al. |
| 6,714,809 B2 | 3/2004 | Lee et al. |
| 6,765,779 B2 | 7/2004 | Stevenson et al. |
| 6,765,780 B2 | 7/2004 | Brendel et al. |
| 6,771,067 B2 | 8/2004 | Kellman et al. |
| 6,829,509 B1 | 12/2004 | MacDonald et al. |
| 6,847,837 B1 | 1/2005 | Melzer et al. |
| 6,868,288 B2 | 3/2005 | Thompson |
| 6,876,885 B2 | 4/2005 | Swoyer et al. |
| 6,882,248 B2 | 4/2005 | Stevenson et al. |
| 6,888,715 B2 | 5/2005 | Stevenson et al. |
| 6,898,454 B2 | 5/2005 | Atalar et al. |
| 6,904,307 B2 | 6/2005 | Karmarkar et al. |
| 6,925,328 B2 | 8/2005 | Foster et al. |
| 6,931,286 B2 | 8/2005 | Sigg et al. |
| 6,949,929 B2 | 9/2005 | Gray et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,993,373 B2 | 1/2006 | Vrijheid |
| 6,999,818 B2 | 2/2006 | Stevenson et al. |
| 7,012,192 B2 | 3/2006 | Stevenson et al. |
| 7,013,180 B2 | 3/2006 | Villaseca et al. |
| 7,031,774 B1 * | 4/2006 | Doan et al. ................. 607/37 |
| 7,038,900 B2 | 5/2006 | Stevenson et al. |
| 7,047,074 B2 | 5/2006 | Connelly et al. |
| 7,092,766 B1 | 8/2006 | Salys et al. |
| 7,113,387 B2 | 9/2006 | Stevenson et al. |
| 7,133,714 B2 | 11/2006 | Karmarkar et al. |
| 7,155,271 B2 | 12/2006 | Halperin et al. |
| 7,236,816 B2 | 6/2007 | Kumar et al. |
| 7,310,216 B2 | 12/2007 | Stevenson et al. |
| 7,363,090 B2 | 4/2008 | Halperin et al. |
| 7,412,276 B2 | 8/2008 | Halperin et al. |
| 7,422,568 B2 | 9/2008 | Yang et al. |
| 7,535,693 B2 | 5/2009 | Stevenson et al. |
| 7,689,288 B2 | 3/2010 | Stevenson et al. |
| 7,751,903 B2 | 7/2010 | Stevenson et al. |
| 7,822,460 B2 | 10/2010 | Halperin et al. |
| 7,844,319 B2 | 11/2010 | Susil et al. |
| 7,853,325 B2 | 12/2010 | Dabney et al. |
| 7,899,551 B2 | 3/2011 | Westlund et al. |
| 7,917,219 B2 | 3/2011 | Stevenson et al. |
| 2002/0040185 A1 | 4/2002 | Atalar et al. |
| 2002/0055678 A1 | 5/2002 | Scott et al. |
| 2002/0095197 A1 | 7/2002 | Lardo et al. |
| 2002/0097050 A1 | 7/2002 | Kellman et al. |
| 2002/0161421 A1 | 10/2002 | Lee et al. |
| 2002/0167315 A1 | 11/2002 | Kellman et al. |
| 2002/0177771 A1 | 11/2002 | Guttman et al. |
| 2002/0192688 A1 | 12/2002 | Yang et al. |
| 2003/0028094 A1 | 2/2003 | Kumar et al. |
| 2003/0028095 A1 | 2/2003 | Tulley et al. |
| 2003/0050557 A1 | 3/2003 | Susil et al. |
| 2003/0179536 A1 | 9/2003 | Stevenson et al. |
| 2003/0199755 A1 | 10/2003 | Halperin |
| 2003/0208252 A1 | 11/2003 | O'Boyle et al. |
| 2003/0213604 A1 | 11/2003 | Stevenson et al. |
| 2003/0213605 A1 | 11/2003 | Brendel et al. |
| 2004/0015079 A1 | 1/2004 | Berger et al. |
| 2004/0024434 A1 | 2/2004 | Yang et al. |
| 2004/0046557 A1 | 3/2004 | Kamarkar et al. |
| 2004/0167392 A1 | 8/2004 | Halperin et al. |
| 2004/0201947 A1 | 10/2004 | Stevenson et al. |
| 2004/0263173 A1 | 12/2004 | Gray |
| 2004/0263174 A1 | 12/2004 | Gray et al. |
| 2005/0197677 A1 | 9/2005 | Stevenson |
| 2005/0219787 A1 | 10/2005 | Stevenson et al. |
| 2006/0009819 A1 | 1/2006 | Przybyszewski |
| 2006/0100506 A1 | 5/2006 | Halperin et al. |
| 2006/0247684 A1 | 11/2006 | Halperin et al. |
| 2006/0259093 A1 | 11/2006 | Stevenson et al. |
| 2007/0019362 A1 | 1/2007 | Stevenson et al. |
| 2007/0088416 A1 | 4/2007 | Atalar et al. |
| 2007/0288058 A1 | 12/2007 | Halperin et al. |
| 2008/0049376 A1 | 2/2008 | Stevenson et al. |
| 2008/0058635 A1 | 3/2008 | Halperin et al. |
| 2008/0065181 A1 | 3/2008 | Stevenson |
| 2008/0116997 A1 | 5/2008 | Dabney et al. |
| 2008/0119919 A1 | 5/2008 | Atalar et al. |
| 2008/0132987 A1 | 6/2008 | Westlund et al. |
| 2008/0269591 A1 | 10/2008 | Halperine et al. |
| 2009/0116167 A1 | 5/2009 | Stevenson et al. |
| 2009/0259265 A1 | 10/2009 | Stevenson et al. |
| 2010/0016936 A1 | 1/2010 | Stevenson et al. |
| 2010/0023000 A1 | 1/2010 | Stevenson et al. |
| 2010/0023095 A1 | 1/2010 | Stevenson et al. |
| 2010/0160997 A1 | 6/2010 | Johnson et al. |
| 2010/0168821 A1 | 7/2010 | Johnson et al. |
| 2010/0174349 A1 | 7/2010 | Stevenson et al. |
| 2010/0191236 A1 | 7/2010 | Johnson et al. |
| 2010/0198312 A1 | 8/2010 | Stevenson et al. |
| 2010/0217262 A1 | 8/2010 | Stevenson et al. |
| 2010/0222857 A1 | 9/2010 | Halperin et al. |
| 2010/0280584 A1 | 11/2010 | Johnson et al. |
| 2010/0321163 A1 | 12/2010 | Stevenson |
| 2010/0324639 A1 | 12/2010 | Stevenson et al. |
| 2011/0022140 A1 | 1/2011 | Stevenson et al. |
| 2011/0040343 A1 | 2/2011 | Johnson et al. |
| 2011/0054582 A1 | 3/2011 | Dabney et al. |

FOREIGN PATENT DOCUMENTS

| | | |
|---|---|---|
| EP | 0466424 A1 | 1/1992 |
| EP | 0557127 A2 | 8/1993 |
| EP | 0 673 621 A1 | 9/1995 |
| EP | 0557127 A3 | 3/1996 |
| EP | 0 498 996 B1 | 3/1997 |
| EP | 1021730 B1 | 4/2003 |
| EP | 0930509 B1 | 3/2004 |
| JP | 61181925 | 8/1986 |
| JP | 4071536 | 3/1992 |
| JP | 6-70902 | 3/1994 |
| JP | 6054823 | 3/1994 |
| JP | 06070902 A | 3/1994 |
| JP | 09094238 A | 4/1997 |
| JP | 11239572 | 9/1999 |
| WO | 87/04080 | 7/1987 |
| WO | 92/10213 | 6/1992 |
| WO | 94/23782 | 10/1994 |
| WO | 97/40396 | 10/1997 |
| WO | 98/52461 A1 | 11/1998 |
| WO | 99/19739 | 4/1999 |
| WO | 00/10456 A1 | 3/2000 |
| WO | 00/25672 | 5/2000 |
| WO | 00/25672 A | 5/2000 |

(56) References Cited

FOREIGN PATENT DOCUMENTS

| WO | 02/083016 A1 | 10/2002 |
|---|---|---|
| WO | 2006/031317 A2 | 3/2006 |

OTHER PUBLICATIONS

Bauemfeind et al., "Chronic Nonparoxysmal Sinus Tachycardia in Otherwise Healthy Persons", Ann. Intern. Med. 91: 702-710 (1979).
Chorro et al,, "Transcatheter Ablation of the Sinus Node in Dogs Using High Frequency Current," European Heart J. 11:82-89 (1990).
Cox et al., "Modification of the Maze Procedure for Atrial Flutter and Atrial Fibrillation, II: Surgical Technique of The Maze in Procedure", J. Thorac. Cardiovasc. Surg. 110: 485-495 (1995).
Edelman et al.; "Magnetic Resonance Imaging," NEJM. 328:708-716 (1993).
Gabriel, C. et al., "The Dielectric Properties of Biological Tissues: Literature Survey," Phys. Med. Biol. 41:2231-2249 (1996).
Gabriel, S. et al., "The Dielectric Properties of Biological Tissues: Measurements and the Frequency Range 10 Hz to 20 GHz," Phys. Med. Biol. 41:2251-2269 (1996).
Gabriel, S. et al., "The Dielectric Properties of Biological Tissues: Parametric Models for the Dielectric Spectrum of Tissues," Phys. Med. Biol. 41:2271-2293 (1996).
Garrey, W.E., "The Nature of Fibrillary Contraction of the Heart—Its Relation To Tissue Mass And Form," Am. J. Physiol.,33: 397-414 (1914).
Garwood et al.; "Magnetic Resonance Imaging with Adiabatic Using a Single Surface Coil for RF Transmission and Signal Detection," Magnetic Resonance in Medicine 9: 25-34 (1989).
Haines et al., "Primary Atrial Fibrillation Ablation (PAFA) In A chronic Atrial Fibrillation Model", Circulation, 92(8): I-265 (#1261) (1995).
Haissaguerre et al. "Spontaneous Initiation of Atrial Fibrillation by Ectopic Beats Originating in the pulmonary Veins," New Engl.-J. Med. 339:659-666 (1998).
Hoult, D. I. et al, "The Signal-To-Noise Ratio of The Nuclear Magnetic Resonance Experiment", Journal of Magnetic Resonance, 24:71-85(1976).
Hoult, D. I., "Rotating Frame Zeugmatography", Phil. Trans. R. Soc. Lond. B., 289, 543-547 (1980).
International Search Report for PCT Application No. PCT/US 03/17085; Sep. 29, 2003.
Jais et al., "A Focal Source Of Atrial Fibrillation Treated By Discrete Radiofrequency Ablation", Circulation, 95:572-576 (1997).
Jolesz et al., "Interventional Magnetic Resonance Therapy," Seminars in Interventional Radiology, 12: 20-27 (1995).
Kalman et al., "Radiofrequency Catheter Modification of Sinus Node Function Guided by Intracardiac Echocardiography," Circulation 192:3070-3081 (1995).
Kalman, J. et al, "Cristal Tachycardia—Relationship of Right Atrial Tachycardias To The Crista Terminalis Identified Using Intracardiac Echocardiography", Pacing and Clinical Electrophysiology, 18, 261 (1995).
Kay, G. et al. "Radiofrequency Ablation for Treatment of Primary Atrial Tachycardias," J. Am. Coll. Cardiol. 21:901-909 (1993).
Kumar, A., "MR Imaging With A Biopsy Needle", Proc. Intl. Soc. Mag. Reson. Med. 9, 2148 (2001).
Lee et al.; "Catheter Modification of the Atrioventricular Junction with Radiofrequency Energy for Control of Atrioventricular Nodal Reentry Tachycardia," Circulation, 83: 827-835 (1991).
Lesh, M. et al., "Radiofrequency Catheter Ablation of Atrial Arrhythmias", Circulation 89,1074-1089 (1994).
Luchinger, R., "Safety Aspects of Cardiac Pacemakers in Magnetic Resonance Imaging," a dissertation submitted to the Swiss Federal Institute of Technology Zurich, Zurich, Switzerland (2002).
Mitchell, M. et al., "Morphologic And Physiologic Characteristics Of Discontinuous Linear Atrial Ablations During Atrial Pacing and Atrial Fibrillation", Pace, 20 vol. 20 (Part II), 202 (1997).
Moe et al.; "Atrial Fibrillation as a Self-Sustaining Arrhythmia Independent of Focal Discharge," American Heart Journal, 58: 59-70 (1959).
Moe, G. K. "On the Multiple Wavelet Hypothesis of Atrial Fibrillation," Arch. Int. Pharmacodyn. Ther. 140:183-199 (1962).
Natale et al.; "Catheter Ablation Approach on the Right side only for Paroxysmal Atrial Fibrillation Therapy", American Heart Association, Circulation, 92(8): 1-266 (1995).
Prystowsky et al. "Management of Patients with Atrial Fibrillation: A Statement for Healthcare Professionals from the Committee on Electrocardiography and Electrophysiology," American Heart Association, Circulation 93 (6):1262-1277 (1996).
Quick, H. H. et al., "Endourethral MRI", Intl. Soc. Mag. Reson. Med., 1, 142 (2000).
Roguin, A. et al., "Modern Pacemaker and Implantable Cardioverter/Defibrillator Systems Can Be Magnetic Resonance Imaging Safe," American Heart Association, Circulation—Journal of the American Heart Association, 475-482, Dallas, Texas, USA (Aug. 4, 2004, originally published online Jul. 26, 2004).
Susil, R., "Interventional MRI: Targeting, Monitoring, and Assessment of Minimally Invasive Therapies," Doctoral Dissertation, Johns Hopkins University, 1-229 (2005).
Swartz, J. et al., "A Catheter-Based Curative Approach To Atrial Fibrillation In Humans," Abstracts From the 67th Scientific Sessions, 1-335: 1794 (1994).
Tracy et al. "Radiofrequency Catheter Ablation of Ectopic Atrial Tachycardia Using Paced Activation Sequence Mapping," J. Am. Coll. Cardio. 21:910-917 (1993).
West, T. et al., "Minimal Mass Required For Induction Of A Sustained Arrhythmia In Isolated Atrial Segments", Am. J. Physiol., 202, 232-236 (1962).
Zimmerman et al., "Artifacts and Hazards in NMR Imaging due to Metal Implants and Cardiac Pacemakers," Diagn. Imag. Clin. Med. 53:53-56 (1984).
Zipes. D., "Atrial Fibrillation: a Tachycardia-Induced Atrial Cardiomopathy," Circulation 95:562-564 (1997).
Official Communication, U.S. Appl. No. 11/932,227, mailed May 20, 2010.
Official Communication, U.S. Appl. No. 11/924,877, mailed Mar. 11, 2010.
U.S. Appl. No. 60/269,817, filed Feb. 20, 2001.
Susil et al. "A Combined Electrophysiology/MR Antenna Catheter" International Society of Magnetic Resonance Imaging in Medicine, Ninth Scientific Meeting, Glasgow 542 (Apr. 2001).
Susil et al "Multifinctional Interventional Devices for MRI: A Combined Electrophysiology/MRI Catheter" Magnetic Resonance in Medicine 47(3): 594-600 (2002).
Atalar et al. "High Resolution Intravascular MRI and MRS using a Catheter Receiver Coil" Magnetic Resonance in Medicine 36:596-605 (1996) Abstract Only.
Chen et al. "Right Atrial Focal Atrial Fibrillation: Electrophysiologic Characteristics and Radiofrequency Cathether Abation" J. Cardiovasc. Electrophysiol. 10(3):328-335 (1999).
Hsieh et al. "Double Multi-electrode Mapping Catheters Facilitate Radiofrequency Catheter Ablation of Focal Atrial Fibrillation Originating From Pulmonary Veins" J. Cardiovasc. Electrophysiol. 10:136-144 (1999).
Kalman et al. "Biophysical Characteristics of Radiofrequency Lesion Formation in Vivo: Dynamics of Catheter Tip-Tissue Contrast Evaluated by Intracardiac Echocardiography" Am. Heart J. 133(1):8-18 (1997).
Karmarkar "An active MRI Intramyocardial Injection Catheter" Proc. Intl. Soc. Mag. Reson. Med. 11:311 (2003).
Ocali et al. "Intravascular Magnetic Resonance Imaging Using a Loopless Catheter Antenna" MRM 37:112-188 (1997).
Silverman et al. "Interactive MR-Guided Biopsy in an Open Configuration MR Imaging System" Radiology 197(1): 175-181 (1995).
Susil "Multifunctional Interventional Devices for MRI: A Combined Electrophysiology/MRI Catheter" Mag. Reson. Med. 47:594-600 (2002).
Official Communication for U.S. Appl. No. 11/560,055 mailed Jun. 27, 2013.

(56) References Cited

OTHER PUBLICATIONS

Official Communication for U.S. Appl. No. 11/560,055 mailed Dec. 1, 2009.
Official Communication for U.S. Appl. No. 11/560,055 mailed Jun. 24, 2009.
Official Communication for U.S. Appl. No. 10/123,534 mailed Mar. 23, 2009.
Official Communication for U.S. Appl. No. 10/123,534 mailed Aug. 30, 2007.
Official Communication for U.S. Appl. No. 10/123,534 mailed Aug. 18, 2006.
Official Communication for U.S. Appl. No. 11/932,227 mailed Mar. 5, 2012.
Official Communication for U.S. Appl. No. 11/932,227 mailed Aug. 23, 2011.
Official Communication for U.S. Appl. No. 11/932,227 mailed Dec. 14, 2010.
Official Communication for U.S. Appl. No. 11/932,227 mailed Aug. 12, 2009.

* cited by examiner

MRI COMPATIBLE MEDICAL LEADS

CROSS-REFERENCE TO RELATED APPLICATIONS

This application is a continuation of U.S. patent application Ser. No. 11/560,055, filed Nov. 15, 2006, now allowed, which is a continuation of U.S. patent application Ser. No. 10/123,534, which issued as U.S. Pat. No. 7,844,319, which claims benefit of priority to U.S. Provisional Patent Application Ser. No. 60/283,725, filed Apr. 13, 2001. The aforementioned applications are incorporated herein in their entireties by this reference.

GOVERNMENT GRANTS

This invention was made, in part, with government support under grant numbers RO1 HL 57483 and RO1 HL61672 from the National Institutes of Health. The United States government has certain rights to this invention.

BACKGROUND

The disclosed systems and methods relate in general to ablation and electrophysiologic diagnostic and therapeutic procedures, and in particular to systems and methods for performing, guiding, and providing visualization of such procedures.

Atrial fibrillation and ventricular tachyarrhythmias occurring in patients with structurally abnormal hearts are of great concern in contemporary cardiology. They represent the most frequently encountered tachycardias, account for the most morbidity and mortality, and, despite much progress, remain therapeutic challenges.

Atrial fibrillation affects a larger population than ventricular tachyarrhythmias, with a prevalence of approximately 0.5% in patients 50-59 years old, increasing to 8.8% in patients in their 80's. Framingham data indicate that the age-adjusted prevalence has increased substantially over the last 30 years, with over 2 million people in the United States affected. Atrial fibrillation usually accompanies disorders such as coronary heart disease, cardiomyopathies, and the postoperative state, but occurs in the absence of any recognized abnormality in 10% of cases. Although it may not carry the inherent lethality of a ventricular tachyarrhythmia, it does have a mortality twice that of control subjects. Symptoms which occur during atrial fibrillation result from the often rapid irregular heart rate and the loss of atrio-ventricular (AV) synchrony. These symptoms, side effects of drugs, and most importantly, thrombo-embolic complications in the brain (leading to approximately 75,000 strokes per year), make atrial fibrillation a formidable challenge.

Two strategies have been used for medically managing patients with atrial fibrillations. The first involves rate control and anticoagulation, and the second involves attempts to restore and maintain sinus rhythm. The optimal approach is uncertain. In the majority of patients, attempts are made to restore sinus rhythm with electrical or pharmacologic cardioversion. Current data suggest anticoagulation is needed for 3 to 4 weeks prior to and 2 to 4 weeks following cardioversion to prevent embolization associated with the cardioversion. Chronic antiarrhythmic therapy may be indicated once sinus rhythm is restored. Overall, pharmacologic, therapy is successful in maintaining sinus rhythm in 30 to 50% of patients over one to two years of follow-up. A major disadvantage of antiarrhythmic therapy is the induction of sustained, and sometimes lethal, arrhythmias (proarrhythmia) in up to 10% of patients.

If sinus rhythm cannot be maintained, several approaches are used to control the ventricular response to atrial fibrillation. Pharmacologic agents which slow conduction through the AV node are that tried. When pharmacologic approaches to rate control fail, or result in significant side effects, ablation of the AV node, and placement of a permanent pacemaker may be considered. The substantial incidence of thromboembolic strokes makes chronic anticoagulation important, but bleeding complications are not unusual, and anticoagulation cannot be used in all patients.

In addition to medical management approaches, surgical therapy of atrial fibrillation has also been performed. The surgical-maze procedure, developed by Cox, is an approach for suppressing atrial fibrillation while maintaining atrial functions. This procedure involves creating multiple linear incisions in the left and right atria. These surgical incisions create lines that block conduction and compartmentalize the atrium into distinct segments that remain in communication with the sinus node. By reducing the mass of atrial tissue in each segment, the mass of atrial tissue is insufficient to sustain the multiple reentrant rotors, which are the basis for atrial fibrillation. Surgical approaches to the treatment of atrial fibrillation result in an efficacy of >95% and a low incidence of complications. However, despite these encouraging results, this procedure has not gained widespread acceptance because of the long duration of recovery and risks associated with cardiac surgery.

Invasive studies of the electrical activities of the heart (electrophysiologic studies) have also been used in the diagnosis and therapy of arrhythmias. Focal atrial tachycardias, AV-nodal reentrant tachycardias, accessory pathways, atrial flutter, and idiopathic ventricular tachycardia can be cured by selective destruction of critical electrical pathways with radiofrequency (RF) catheter ablation. Electrophysiologists have attempted to replicate the maze procedure using RF catheter ablation. The procedure is arduous, requiring general anesthesia and procedure durations often greater than 12 hours, with exposure to ionizing x-ray irradiation for over 2 hours. Some patients have sustained cerebrovascular accidents. One of the main limitations of the procedure is the difficulty associated with creating and confirming the presence of continuous linear lesions in the atrium. If the linear lesions have gaps, then activation can pass through the gap and complete a reentrant circuit, thereby sustaining atrial fibrillation or flutter. This difficulty contributes significantly to the long procedure durations discussed above.

Creating and confirming continuous linear lesions and morbidity could be facilitated by improved minimally-invasive techniques for imaging lesions created in the atria. Such an imaging technique may allow the procedure to be based purely on anatomic findings.

The major technology for guiding placement of a catheter is x-ray fluoroscopy. For electrophysiologic studies and ablation, frame rates of 7-15 per second are generally used which allows an operator to see x-ray-derived shadows of the catheters inside the body. Since x-rays traverse the body from one side to the other, all of the structures that are traversed by the x-ray beam contribute to the image. The image, therefore is a superposition of shadows from the entire thickness of the body. Using one projection, therefore, it is only possible to know the position of the catheter perpendicular to the direction of the beam. In order to gain information about the position of the catheter parallel to the beam, it is necessary to use a second beam that is offset at some angle from the original beam, or to move the original beam to another angular position. Since x-ray shadows are the superposition of contributions from many structures, and since the discrimination of different soft tissues is not great, it in often very difficult to determine exactly where the catheter is within the heart. In addition, the borders of the heart are generally not accurately defined, so it is generally not possible to know if the catheter has penetrated the wall of the heart, and lesions are invisible under x-ray fluoroscopy. Thus, it is very difficult to discern whether tissue has been adequately ablated. The intracardiac electrogram may be used to guide the catheters to the proper cardiac tissue.

Intracardiac ultrasound has been used to overcome deficiencies in identifying soft tissue structures. With ultrasound it is possible to determine exactly where the walls of the heart are with respect to a catheter and the ultrasound probe, but the ultrasound probe is mobile, so there can be doubt where the absolute position of the probe is with respect to the heart.

Neither x-ray fluoroscopy nor intracardiac ultrasound have the ability to accurately and reproducibly identity areas of the heart that have been ablated.

A system known as "non-fluoroscopic electro-anatomic mapping" (U.S. Pat. No. 5,393,199 to Ben-Haim), was developed to allow more accurate positioning of catheters within the heart. That system uses weak magnetic fields and a calibrated magnetic field detector to track the location of a catheter in 3-space. The system can mark the position of a catheter, but the system relies on having the heart not moving with respect to a marker on the body. The system does not obviate the need for initial placement using x-ray fluoroscopy, and cannot directly image ablated tissue.

Magnetic resonance imaging (MRI) is a known imaging technique which uses high-strength magnetic and electric fields to image the body. A strong static magnetic field orients the magnetic moments of the hydrogen nuclei creating a bulk nuclear magnetization. RF magnetic field pulses with frequency tuned to the resonant or "Larmor" frequency in the presence of the static field, change the spatial orientation of the bulk magnetization of the nuclei, as known to those skilled in the art. In addition, time-varying gradient magnetic fields applied in the three Cartesian directions (X, Y, Z) are used for spatial encoding of the signals from the tissue. The magnitude of a gradient magnetic field is such as to cause the main static magnetic field to vary linearly as a function of the respective spatial coordinate in the magnet. As a result of the addition of the static and gradient magnetic fields, the local Larmor resonance frequency, is spatially encoded. The information corresponding to the strength of the magnetization at each point in space can then be decoded by means of reconstruction techniques known to those skilled in the art, permitting the imaging of tissues in three-dimensional space.

MRI has been used to guide procedures in which RF energy is applied to non-contractile organs such as the brain, liver and kidneys to ablate tumors. However, these systems are not suitable for use in the heart. U.S. Pat. No. 5,323,778 to Kandarpa et al. discloses a method and apparatus for MRI and tissue heating. There is no provision in the disclosed probe for measuring electrical signals, and it is unclear how much resolution is provided by the probe.

SUMMARY

The systems and methods disclosed herein enhance the art by, among other things, facilitating the performance of multiple functions during electrophysiological interventions with MRI. An embodiment provides an instrument that can be easily visualized and/or tracked in an MR or other image. An embodiment provides an instrument that can be easy to maneuver. An embodiment provides an instrument that can facilitate high resolution imaging of a target area. An embodiment provides an instrument that can record an intracardiac electrogram. An embodiment provides an instrument that can deliver RF energy for ablation of the desired tissue near the instrument tip.

An embodiment provides an improved multi-functional systems and methods for guiding and/or providing visualization during electrophysiologic procedures.

In an embodiment, the disclosed systems and methods facilitate guiding or visualizing ablation procedures suitable for use in, e.g., the heart and other structures.

In an embodiment, the disclosed systems and methods include catheters that are easy to maneuver and/or track.

In an embodiment, the disclosed systems and methods facilitate imaging ablation lesions with increased resolution of the target area and reliability.

In an embodiment, the disclosed systems and methods facilitate delivering RF energy for ablation of tissue, including but not limited to pathologic tissue.

In an embodiment the disclosed systems and methods facilitate recording and monitoring electrical potentials, including but not limited to physiologic bio-potentials.

In an embodiment, the disclosed systems and methods facilitate determining the position of, e.g., target tissue or an ablation instrument.

In an embodiment, the disclosed systems and methods facilitate guiding the delivery of RF ablation energy.

In an embodiment, the disclosed systems and methods facilitate the integration of imaging and ablation in a single instrument.

In an embodiment, the disclosed systems and methods facilitate using magnetic resonance imaging to increase the safety and accuracy of electrophysiologic procedures.

In an embodiment, the disclosed systems and methods provide an invasive multi-functional electrophysiology and imaging antenna catheter which includes an RF antenna for receiving magnetic resonance signals, a loop antenna for device tracking, an ablation tip for delivering RF energy for ablation procedures, and diagnostic electrodes for receiving physiological electrical potentials. The combined electrophysiology and imaging antenna catheter can be used in combination with a MRI scanner to, for example, guide, perform, and/or provide visualization during electrophysiologic diagnostic or therapeutic procedures.

In an embodiment, the disclosed systems and methods can be particularly applicable to ablation of atrial and ventricular arrhythmias, and in such embodiments may be used as an intracardiac device to both deliver energy to selected areas of tissue and visualize the resulting ablation lesions, thereby greatly simplifying production of continuous linear lesions. Additionally, the disclosed systems and methods can be used as active tracking devices by means of a "loop antenna" that receives MRI signals excited by the scanner. Gradient echoes are then generated along three orthogonal axes to frequency encode the location of the coil and thus provide the three-dimensional (3D) space coordinates of the electrode tip. These numeric coordinates can then be used to control the imaging plane of the scanner, thereby allowing accurate imaging slices to be prescribed to target anatomy for RF therapy. Low resolution images can be obtained indicating catheter location relative to the body by combining the MRI signals from the loop with those of the conventional external MRI detector coil. In addition, high resolution images can be obtained using the signals from the loop antenna. In another embodiment, the loop antenna utilized in the combined electrophysiology and imaging catheter for receiving MRI signals is connected to form a "loopless" type antenna. High-resolution images front the antenna may be combined with low-resolution images from surface coils of the MR scanner to produce a composite image. The disclosed systems and methods further include embodiments useful for guiding electrophysiologic diagnostic and therapeutic procedures other than ablation. An RF filtering system is provided for suppressing the MRI signal while not attending the RF ablative current. Steering means may be provided by steering the invasive catheter under MR guidance. Steering could be facilitated by proving a probe with a pull wire. In addition, the disclosed systems and methods include acquisition of local physiological bio-potential measurements using a multi-electrode catheter, which permits, via MRI guidance, active tracking of the location of each electrode. A central novel feature of the disclosed systems and methods is that because bio-potentials, RF ablation, and MRI are each performed over different frequency ranges, frequency-dependant circuit elements can be used to change the catheter's electrical structure enabling it to provide multiple electrical structures within a single physical structure.

In an embodiment, a probe or catheter includes a first electrode disposed at least partially on the probe surface, a second electrode disposed at least partially on the probe surface, a first conductor electrically coupled to the first electrode, a second conductor electrically coupled to the second electrode, and a reactive element electrically coupling the first conductor and the second conductor.

In an embodiment, a magnetic resonance imaging probe includes a coaxial cable having an inner conductor and an outer shield, a first split ring electrode electrically coupled to the inner conductor, and a second split ring electrode electrically coupled to the outer conductor, a first center split ring electrode electrically coupled to the first split ring electrode and to a first conductor, a second center split ring electrode electrically coupled to the first center split ring electrode and to the second split ring electrode, and also coupled to a second conductor.

In an embodiment, a magnetic resonance imaging probe includes a first electrode disposed on the probe surface, a second electrode disposed on the probe surface, a first conductor electrically coupled to the first electrode through a reactance, a second conductor electrically coupled to the second electrode through a reactance, and a frequency-dependent reactive element electrically coupling the first conductor and the second conductor, such that high-frequency energy is conducted between the first conductor and the second conductor.

In an embodiment, a system for magnetic resonance imaging includes a magnetic resonance imaging probe, having a first electrode disposed on the probe surface, a second electrode disposed on the probe surface, a first conductor electrically coupled to the first electrode through a reactance, a second conductor electrically coupled to the second electrode through a reactance, and a frequency-dependent reactive element electrically coupling the first conductor and the second conductor, such that high-frequency energy is conducted between the first conductor and the second conductor; and an interface electrically coupled to the probe, the interface having a tuning/matching/decoupling circuit and a signal splitting circuit; and an MRI scanner electrically coupled to the interface.

In an embodiment, a magnetic resonance imaging probe includes a coaxial cable having an inner conductor and an outer shield, and a split ring electrode having a first portion and a second portion, the first portion being electrically coupled to the inner conductor, and the second portion being electrically coupled to the outer shield.

In an embodiment, a magnetic resonance imaging probe may include a coaxial cable having an inner conductor and an outer shield, a first split ring electrode electrically coupled to the inner conductor, and a second split ring electrode electrically coupled to the outer conductor; wherein the first split ring and the second split ring are electrically coupled by a first reactive element.

In an embodiment, the reactive element can conduct a high frequency signal between the first conductor and the second conductor. In an embodiment, the high frequency signal has a frequency higher than about 10 MegaHertz (MHz). In an embodiment, the reactive element can conduct a signal having magnetic resonance imaging frequency energy between the first conductor and the second conductor.

In an embodiment, at least one of the first conductor and the second conductor can conduct a low frequency signal to at least one of the first electrode and the second electrode. In an embodiment, the low frequency signal has a frequency of up to about 500 kiloHertz (kHz). In an embodiment, the low frequency is in the range from about 100 Hertz (Hz) to about 1 kHz. In an embodiment, the frequency is about 100 kHz.

In an embodiment, the reactive element conducts a signal having ablation frequency energy to at least one of the first electrode and the second electrode. In an embodiment, the reactive element conducts a signal having biopotential recording frequency energy to at least one of the first electrode and the second electrode.

In an embodiment, the probe further comprises a lumen.

In an embodiment, the reactive element comprises at least one of a high-pass filter, a low-pass filter, a band-pass filter, and a capacitor. In an embodiment, the reactance comprises at least one of an inductor and an LC circuit.

In an embodiment, the first conductor couples to the first electrode through a reactance. In an embodiment, at least one of the first conductor, the second conductor, the first electrode, and the second electrode comprises at least one of a magnetic resonance compatible material, a superelastic material, copper, gold, silver, platinum, iridium, MP35N, tantalum, titanium, Nitinol, L605, gold-platinum-iridium, gold-copper-iridium, and gold-platinum.

In an embodiment, the first conductor and the second conductor are electrically coupled to a tuning/matching/decoupling circuit. In an embodiment, the first conductor and the second conductor are electrically coupled to a signal splitting circuit. In an embodiment, the first conductor and the second conductor are electrically coupled by at least one capacitor.

An embodiment may further include a third conductor electrically coupled to a third electrode, and a fourth conductor electrically coupled to a fourth electrode, wherein a first signal having high frequency energy is conducted between the first conductor and the second conductor through the reactive element, and a second signal having low frequency energy is conducted to at least one of the third electrode and the fourth electrode.

An embodiment may further include a shaft, the shaft including at least one of Kevlar, nylon, Teflon, polyethylene, polyolefin, PTFE, polyurethane, PEBAX, braided Kevlar, and braided nylon. In an embodiment, the probe surface in covered by a lubricious coating.

In an embodiment, the probe has an outer diameter in the range of about 1 French to about 15 French. In an embodiment, the probe has a length in the range of about 50 cm to about 200 cm. In an embodiment, the probe further comprises a pull wire.

In an embodiment, the first conductor, the reactive element, and the second conductor form a loop antenna. In an embodiment, the first conductor, the reactive element, and the second conductor form a loopless antenna.

In an embodiment, the inner conductor and the outer shield are electrically coupled by a reactive element. In an embodiment, the reactive element comprises at least one of a high-pass filter, a low-pass filter, a band-pass filter, and a capacitor. In an embodiment, the inner conductor and the outer shield are electrically coupled by a second reactive element. In an embodiment, the second reactive element comprises at least one of a high-pass filter, a low-pass filter, a band-pass filter, and a capacitor. In an embodiment, the first reactive element comprises at least one of a high-pass filter, a low-pass filter, a band-pass filter, and a capacitor.

In an embodiment, a method for simultaneously imaging and ablating a tissue can include exposing the tissue to a magnetic field, the field having a static component and a gradient component, placing a probe adjacent to the tissue, the probe including a first electrode disposed at least partially on the probe surface, a second electrode disposed at least partially on the probe surface, a first conductor electrically coupled to the first electrode, a second conductor electrically coupled to the second electrode, and a frequency-dependent reactive element electrically coupling the first conductor and the second conductor, such that high-frequency energy is conducted between the first conductor and the second conductor, and low frequency energy is conducted to at least one of the first electrode and the second electrode; directing low-frequency energy to the probe, the low frequency energy being conducted to the tissue by at least one of the first electrode and the second electrode; and receiving high-frequency energy from at least one of the first conductor and the second conductor for imaging at least one of the probe and the tissue.

In an embodiment, a method for simultaneously imaging a tissue and measuring a bioelectric potential in the tissue may include exposing the tissue to a magnetic field, the field having a static component and a gradient component, placing a probe adjacent to the tissue, the probe including a first electrode disposed at least partially on the probe surface, a second electrode disposed at least partially on the probe surface, a first conductor electrically coupled to the first electrode, a second conductor electrically coupled to the second electrode, and a frequency-dependent reactive element electrically coupling the first conductor and the second conductor, such that high-frequency energy is conducted between the first conductor and the second conductor, and low frequency energy is conducted to at least one of the first electrode and the second electrode; receiving low-frequency energy from the probe, the low frequency energy being conducted from at least one of the first electrode and the second electrode; and receiving high-frequency energy from at least one of the first conductor and the second conductor for imaging at least one of the probe and the tissue.

In an embodiment, a method for simultaneously imaging a tissue, ablating the tissue, and measuring a bioelectric potential in the tissue may include exposing the tissue to a magnetic field, the field having a static component and a gradient component, placing a probe adjacent to the tissue, the probe including a first electrode disposed at least partially on the probe surface, a second electrode disposed at least partially on the probe surface, a first conductor electrically coupled to the first electrode, a second conductor electrically coupled to the second electrode, and a frequency-dependent reactive element electrically coupling the first conductor and the second conductor, such that high-frequency energy is conducted between the first conductor and the second conductor, and low-frequency and medium-frequency energy is conducted to at least one of the first electrode and the second electrode; receiving low-frequency energy from the probe, the low frequency energy being conducted from at least one of the first electrode and the second electrode, directing medium-frequency energy to the probe, the medium-frequency energy being conducted to the tissue by at least one of the first electrode and the second electrode, and receiving high-frequency energy from the probe, the high-frequency energy having magnetic resonance imaging data.

In an embodiment, a method for simultaneously imaging and treating a tissue may include exposing the tissue to a magnetic field, the field having a static component and a gradient component, placing a probe adjacent to the tissue, the probe including a first electrode disposed at least partially on the probe surface, a second electrode disposed at least partially on the probe surface, a first conductor electrically coupled to the first electrode, a second conductor electrically coupled to the second electrode, and a frequency-dependent reactive element electrically coupling the first conductor and the second conductor, such that high-frequency energy is conducted between the first conductor and the second conductor; delivering a therapy to the tissue, and receiving high-frequency energy from the probe, the high-frequency energy having magnetic resonance imaging data.

In an embodiment, the therapy may include at least one of ablation energy, heat, ultrasound energy, a substance discharged through a lumen of the probe, and monitoring the delivering.

BRIEF DESCRIPTION OF THE DRAWINGS

Embodiments of the disclosed systems and methods will be apparent from the following more particular description of preferred embodiments as illustrated in the accompanying drawings, in which some reference characters refer to the same parts throughout the various views. The drawings are not necessarily to scale, emphasis instead being placed upon illustrating principles of the disclosed systems and methods.

DETAILED DESCRIPTION

Figure 1A:
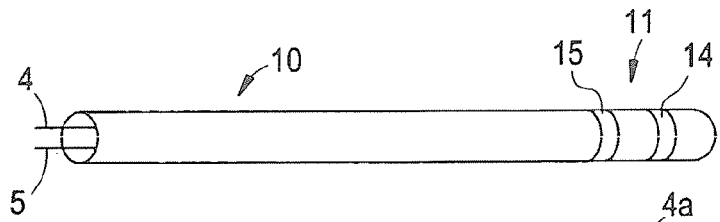
FIGS. 1A-1G show physical and electrical diagrams of a probe or catheter.

The disclosed systems and methods in an embodiment use MRI to allow multi-functional catheters to be placed without radiation, and provides very accurate localization of catheter tips in 3D space. With current MRI scanners, resolution is limited by the distance the RF coil is from the volume of tissue being imaged. The signal from any particular imaging volume is picked up by an external detector coil. The gradients select a volume inside the body for imaging, but the coil outside the body picks up the signal from the imaging volume as well as the noise from all of the sample regions that are within its range. The farther the surface coil is from the imaging volume, the more noise can be present.

MRI has been proposed as an alternative imaging modality for guiding and monitoring EP procedures and offers several advantages over other modalities for electrophysiologic intervention. For example, the heart and endocardial landmarks can be visualized throughout the procedure. This anatomical information facilitates the identification of ablation sites for arrhythmias such as atrial flutter and fibrillation. In addition, cardiac motion and flow dynamics can be monitored during the procedure. This enables acute assessment of cardiac function as the intervention is performed. Furthermore, MRI does not employ ionizing radiation, such as x-rays, and is generally considered to be a minimal risk procedure.

MRI can facilitate the visualization of ablated tissue during the procedure. Because lesions are typically invisible under x-ray fluoroscopy, it is currently difficult to discern whether tissue has been completely ablated, is only temporarily stunned (i.e., has been subjected to reversible thermal injury), or indeed has not been treated at all. By actually visualizing the tissue lesion, MRI enables positive confirmation of tissue treatment. This can be especially important for procedures that benefit from continuous lines of ablation, such as treatment for atrial flutter, atrial fibrillation, and isolation of pathologic tissue in the pulmonary veins. Imaging of ablated tissue may allow what are now long and difficult procedures to be performed on a more routine and efficient basis.

In an embodiment, an internal catheter receiving coil/antenna may be incorporated into an electrophysiologic RF ablation catheter that also includes electrodes for recording bio-potentials. Because the receiving coil/antenna is closer to the imaging volume being targeted for ablation and may have a limited range of detection, the MRI signal is increased and the noise from remote regions reduced, thereby providing an enhanced signal-to-noise ratio (SNR), which enables higher strength MRI gradients to be applied, thereby improving resolution where it is needed most.

In an embodiment, MRI can be used to facilitate catheter ablation of atrial fibrillation by guiding creation of continuous linear ablation lesions, and confirming that a complete linear lesion has been created (line of block) in combination with measurements of bio-potential. The visualization of areas of ablation and measurements of bio-potential may allow a reduction in the number of lesions needed, and may also reduce the number of recurrences, by more accurately ablating the arrhythmias.

A reactive element can include an electrical component such as a capacitor, a resistor, an inductor, a diode, or various combinations of these. A reactive element can be a filter, such as a lowpass filter, a highpass filter, a bandpass filter, or a bandstop filter. A reactance can be a reactive element.

A high frequency signal or high frequency energy can include energy that has a frequency of 10 MegaHertz (MHz) or higher. It can include energy that has a frequency of 60 MHz or higher. It can include energy that has a frequency of about 63.9 MHz.

A low frequency signal or low frequency energy can include energy that has a frequency of less than 10 MHz. It can include energy that has a frequency of 500 kiloHertz (kHz) or less. It can include energy that has a frequency of 100 kHz or less. It can include energy that has a frequency of 1 kHz or less. It can include energy that has a frequency of 100 Hertz (Hz) or less.

Ablation frequency energy can include energy that has a frequency of less than 10 MHz. It can include energy that has a frequency of 500 kiloHertz (kHz) or less. It can include energy that has a frequency of 100 kHz or less. It can include energy that has a frequency of 1 kHz or less. It can include energy that has a frequency of 100 Hertz (Hz) or less.

Biopotential recording frequency energy can include energy that has a frequency of less than 10 MHz. It can include energy drat has a frequency of 500 kiloHertz (kHz) or less. It can include energy that has a frequency of 100 kHz or less. It can include energy that has a frequency of 1 kHz or less. It can include energy that has a frequency of 100 Hertz (Hz) or less. It can include energy that has a frequency between about 100 Hz and about 1 kHz.

Medium frequency energy can include energy that has a frequency of less than 10 MHz and greater that 50 kHz. It can include energy that has a frequency between 500 kiloHertz (kHz) and 50 kHz. It can include energy that has a frequency between 200 kHz and 50 kHz. It can include energy that has a frequency of 100 kHz.

A catheter can be a probe. A probe can be a catheter.

In an embodiment, a lubricious material can include at least one of polyvinylpyrrolidone, polyacrylic acid, hydrophilic substance, or silicone.

Figure 1B:
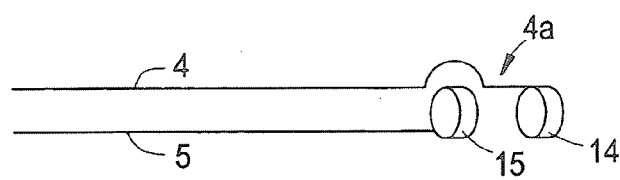

FIG. 1A depicts the physical structure of a probe or catheter according to an embodiment. A probe 10 can be about 10 cm to about 1000 cm long. The probe 10 can be from about 50 cm to about 200 cm long. The probe can be 100 cm long. The probe 10 can be a catheter. The probe 10 may have two surface electrodes 14, 15. The surface electrodes 14, 15 may be ring electrodes. The, are located at the distal end, 15, and two wire leads, 4 and 5, run the length of the catheter. The electrical structure of a conventional electrophysiology catheter is shown in FIG. 1b. Note that the electrical leads 4 and 5, terminate in respective surface electrodes, 14 and 15. This arrangement can be less preferred for MRI studies because of (i) potential safety issues arising from heating induced in the wires and electrodes by the MRI excitation field; (ii) application of RF energy for ablation may result in significant degradation and interference during MRI scanning; and (iii) the elements are not tuned to the MRI frequency and generally will not provide improved SNR and MRI resolution performance. Interfering signals and noise not related to MRI detection should be limited, as should be currents induced directly in the conductors by the time-dependent MRI fields. MRI tracking may be facilitated be creating a small, configured region of high SNR.

It is known to those skilled in the art that long, flexible loop antennas produce local regions of high signal and are therefore ideal for active catheter tracking (For example, see Atalar E, Bottomley P A, Ocali O, Correia L C, Kelemen M D, Lime J A, Zerhouni E A. High resolution intravascular MRI and MRS by using a catheter receiver coil. Magn Reson Med. 1996;36:596-605). For a catheter structure with two electrical leads, a loop antenna configuration can be produced by short-circuiting the distal end of the catheter. While this solution may be theoretically ideal, it is unacceptable for electrophysiology interventions because in order to perform ablation and to record of bio-potentials, multiple, electrically isolated wire leads are preferred.

Figure 1C:
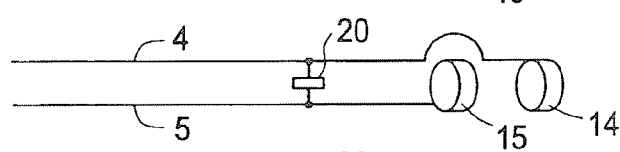

In an embodiment, a capacitor 20, is placed at the distal end 11, of the catheter (FIG. 1c). In another preferred embodiment, in addition to the capacitor 20 at the distal end of the catheter, RF reactances 24 and 25 are applied in series with each of the surface electrodes 14 and 15, in order to improve the safety of the device for MRI applications. The component values of the reactances 24 and 25 are adjusted or tuned such as to produce a high impedance at the MRI frequency, but low impedance at the frequency used for RF ablation and/or measuring bio-potentials. More specifically, in one embodiment each of the reactances 24 and 25 may include a non-magnetic RF inductor. In another preferred embodiment, each of the reactances 24 and 25 may include an RF inductor-capacitor pair, preferably non-magnetic, connected in parallel to form a parallel resonant LC circuit with resonant tuned to substantially equal to the MRI frequency, for example, 63.9 MHz with a static magnetic field of 1.5 Tesla. By this means each LC pair provides a high impedance at the MRI frequency. The LC circuit can be formed by winding a wire coil around a ceramic chip capacitor. For maximum effectiveness, the LC circuit should be shielded with conducting foil or the like.

Figures 1, 1C:
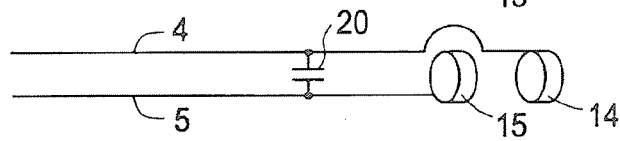

To understand the function of the catheter, it is useful to consider the electrical appearance of the device at both low and high frequency ranges. First, at low frequencies, the capacitor has a large impedance and behaves approximately as an open circuit. The RF inductors have low impedance and appear as short circuits. Therefore, the low frequency structure (FIG. 1d) of the catheter behaves the same as the conventional structure (FIG. 1a). The electrodes can thus be used for monitoring bio-potentials, and applying RF ablation at frequencies, for example, that are lower than the MRI frequency (for example, less than about 15 MHz for RF ablation vs 63.9 MHz for MRI at 1.5 Tesla). However, at high frequencies or at the MRI frequency, the structure is quite different. The impedance of the capacitor at high frequencies is small and is depicted as a short circuit, 21 in FIG. 1e. The RF inductors have a large impedance, behaving approximately as open circuits 34, 35. Note that the use of LC resonant reactances 24 and 25 can provide a much higher impedance at the MRI frequency, depending on the circuit Quality factor (Q). The net result is that rather than a two-lead catheter, the catheter now acts as a long loop MRI receiver, 40, which is ideal for tracking. Furthermore, the two catheter electrodes, 14, 15 have been decoupled from the rest of the circuit as depicted in FIG. 1e. Note that the two electrical structures shown in FIG. 1d and FIG. 1e exist simultaneously, but at different frequency ranges. Therefore, this structure enables the same leads to be used for high resolution MR Imaging, the recording of physiological potentials, and/or RF ablation.

Figures 1, 1C, 2:
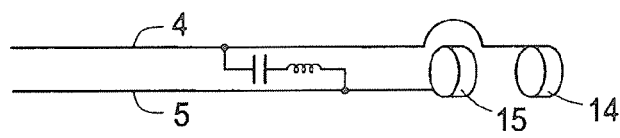
Figures 1, 1C, 2, 3:
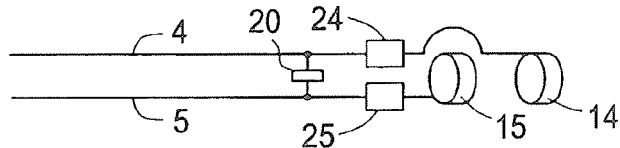
FIG. 3 shows a block diagram illustrating a system for magnetic resonance imaging.
Figure 1D:
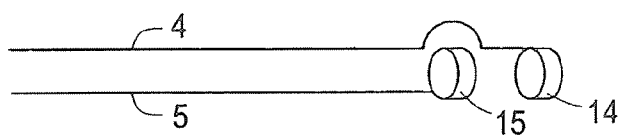
Figure 1E:
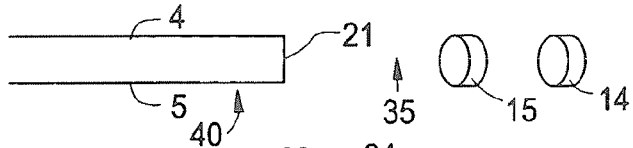
Figure 1F:
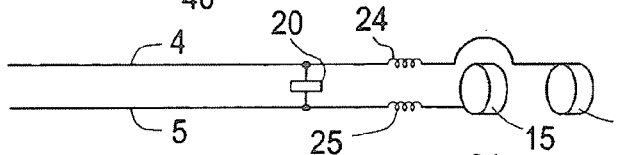
Figure 1G:
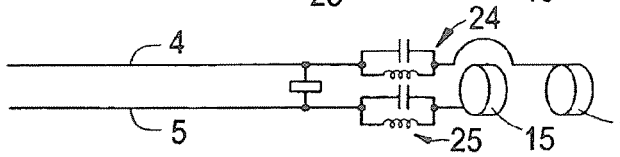
Figure 2A:
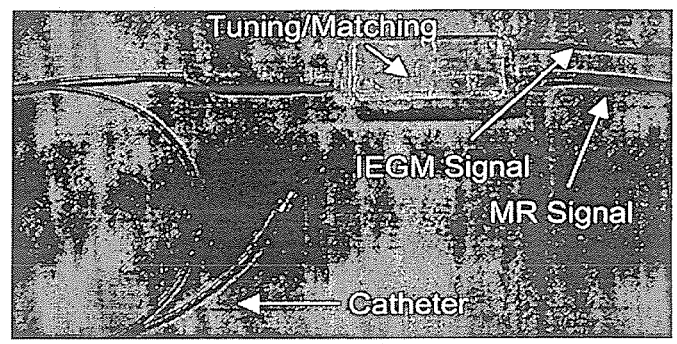
FIGS. 2A-2I show physical and electrical diagrams of a probe or catheter and of an interface.

In the preferred embodiment, the proximal ends 4 and 5 of the catheter are connected to an MRI tuning, matching and decoupling circuit 99 and signal splitting circuit 100 as exemplified in FIG. 2. FIG. 2a shows a photograph of the circuitry in a prototype system. In the MRI tuning, matching and decoupling circuit 99 (FIG. 2b), reactive elements 70, 71, 74, and 77 are providing such that the catheter loop 40 shown electrically in FIG. 1e and which has an electrical inductance, is tuned to resonate at the MRI frequency when the catheter is engaged in the sample of interest such as the body. In addition, the reactive elements are adjusted so that time impedance at the catheter MRI output connections 84 and 85 is matched approximately to the characteristic impedance of the transmission cable used to connect the catheter to the receiver input of the MRI system. For example, 50Ω coaxial cable with BNC type connectors. Alternatively, the catheter MRI output connections 84 and 85 can be connected directly to the receiver input of the MRI system, for example, to the input of a preamplifier. In this case, the impedance should be adjusted to the value that corresponds to the preamplifier input impedance that results in an optimum or near-optimum preamplifier noise figure.

Figure 2B:
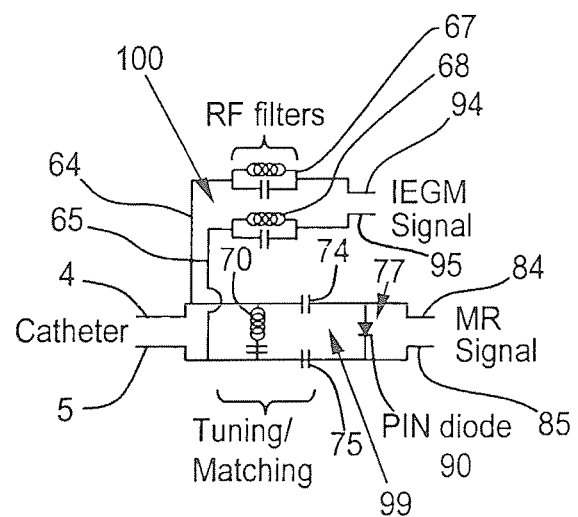

It will be understood that the matching circuit shown in FIG. 2b has the advantage of providing a balanced input, analogous to that provided by a balun transformer, by virtue of the two capacitors 74 and 75 connected to both sides of the catheter leads. Suitable tuning and matching circuits for catheter devices are known to those skilled in the art, for example, as described in Atalar et al cited above, and in Ocali O, Atalar E. entitled "Intravascular magnetic resonance imaging using a loopless catheter antenna" in *Magn Reson Med.* 1997;37: 112-8, and it will be understood that other matching and tuning circuits that are routinely used for matching and tuning MRI detector coils may be alternatively used and are within the scope of, and forseen by, the disclosed systems and methods.

In addition, the MRI tuning, matching, decoupling and signal splitting circuit (FIG. 2B) shows, e.g., decoupling element 90 including a low noise PIN diode, connected across the output conductors 84 and 85. During MRI excitation by an external transmit coil, a DC bias voltage is provided by the MRI scanner across the coil input causing the PIN diode to conduct. During conduction, the tuning elements are shorted-out, which results in detuning of the catheter loop 40, and high impedance, thereby limiting those RF currents induced at the MRI frequency in the loop.

In previous studies, concerns have been raised about the safety of using metallic structures in MR scanners. Radiofrequency energy (MHz)—transmitted from the scanner in order to generate the MR signal—can be deposited around the interventional device. This results in high electrical fields around the instrument and local tissue heating. This heating tends to be most concentrated at the ends of the electrical structure. This safety issue can be addressed using the disclosed systems and methods. The concern is that the surface ring electrodes, which directly contact the tissue, can cause local tissue burns. The electrodes need to be cut/removed from the circuit in the megahertz frequency range. This can be accomplished with an inductor circuit element (placed in series) between the lead wires and the surface electrodes. With this design, the electrical end of the leads (in the megahertz range) are buried inside of the catheter and as a result, the concentrated electric fields are also located inside of the catheter, instead of in the tissue. This results in a significant reduction in unwanted tissue heating. A more effective way to 'cut' the surface electrodes from the rest of the circuit could be to use a resonant circuit in place of the inductors. This resonant circuit could include an inductor in parallel with a capacitor (an 'LC circuit'). If this LC circuit is tuned to the MR frequency, it can present a very high impedance at this frequency. This can effectively cut the surface electrodes and reduce unwanted heating. For maximal effectiveness, the LC circuit should be shielded. The LC circuit may be placed distal to the electrodes and allowing the electrodes to be visualized.

In order to monitor physiologic bio-potentials and/or deliver RF energy for ablation, a splitting circuit is required. In FIG. 2b, leads 64 and 65 of splitting circuit 100 are connected across the catheter output leads 4 and 5. These leads are connected via RF filters 67 and 68 to either the bio-potential monitoring device and/or the RF energy source for ablation at 94 and 95. The purpose of RF filters 67 and 68 is to prevent spurious electrical noise signals that are at least at or near the MRI frequency, from passing from either the bio-potential monitoring device or the RF energy source for ablation to the catheter system 40. In addition the RF filters can stop RF signals induced by the MRI scanner, for example during excitation, from being input to the bio-potential monitoring device or the RF ablation energy source. The RF filters 67 and 68 can be of a number of types known to those skilled in the art, including but limited to those described in U.S. patent application Ser. No. 09/428,090, filed Nov. 4, 1999, of which this application is a continuation in part, and in Lardo A C, McVeigh E R, Jumrussirikul P, Berger R D, Calkins H, Lima J, Halperin H R, "Visualization and temporal/spatial characterization of cardiac radiofrequency ablation lesions using magnetic resonance imaging", *Circulation* 2000;102: 698-705. For example, RF filters 67 and 68 can be low pass filters with a cut-off frequency chosen to lie between the MRI frequency of the catheter loop 40, and a lower RF frequency of the RF ablation device so that any signals that arise at the MRI frequency on lines 64 and 65 are significantly attenuated and effectively eliminated. Alternatively, in another preferred embodiment as illustrated in FIG. 2b, filters 67 and 68 are parallel LC resonant circuits with resonant frequencies adjusted to substantially match that of the MRI frequency. By this means, the impedance of each filter can be rendered a very high value at the MRI frequency depending on the Q of the circuit, thereby stopping or substantially eliminating signals arising on lines 64, 65, 94, 95.

In summary, it will be seen that, with the filtering and connections in place as described, low frequency physiological bio-potentials can pass unimpeded from surface electrodes 14 and 15 to bio-potential measuring device connected at outputs 94 and 95. Similarly RF energy for ablation applied at a frequency that is different from the MRI frequency to leads 94 and 95, can be delivered unimpeded to electrodes 14 and 15 when they are used for ablation. Any noise or other signals present at the MRI frequency can be substantially attenuated or effectively eliminated from lines 64, 65, 94, 95. From the MRI standpoint, electrodes 14 and 15 are deactivated and disconnected. The catheter behaves as a loop antenna 40 tuned to the MRI frequency and matched to the MRI system input, 84 and 85. During MRI excitation, or in fact at any point during the procedure when it is desirable to do so, the antenna can be deactivated by a DC bias voltage applied across inputs 84, 85, by virtue of the decoupling means 90.

In this embodiment it will be apparent also that the entire area of the loop antenna 40 extending from the distal portion of the catheter 11 near the electrodes, to the points where the catheter is connected to the MRI tuning, matching, decoupling and splitting circuits 99 and 100, is MRI active. However, a number of situations may arise where it is desirable to limit the length of sensitivity and/or improve the tuning properties of the loop antenna. In particular, the loop 40 is tuned by capacitor 20 in conjunction with the tuning and matching elements 71, 74, and 75 in tuning and matching circuit 99 at each end of a catheter that may be 100 cm or more long. The extended length of this loop may render it susceptible to stray capacitance arising between the leads of the catheter, 4 and 5, and the surrounding sample and/or environment. The effect of this stray capacitance is generally to add capacitance to the effective LC resonant circuit formed by the loop antenna. If the detuning produced by this effect is significant, it is preferably offset by re-adjustment of the tuning and matching circuit 99. Under situations where the catheter is inserted to different lengths in the sample, different amounts of stray capacitance may occur resulting in variable performance and/or a need for retuning which is not convenient during a procedure or study. In addition there are losses associated with the stray capacitances which can degrade performance as an MRI antenna.

In an embodiment, the effect of the stray capacitance is reduced relative to the total capacitance needed to tune the circuit by adding additional capacitance at other locations. In order not to impede passage of bio-potential and/or RF ablation signals, the capacitors are placed between leads 4 and 5 analogous to capacitor 20. In one embodiment, depicted in FIG. 2C, tuning capacitor 20' is connected across 4 and 5 creating distal portions 4" and 5" and proximal portions 4' and 5'. The entire loop 40 is tuned to resonance via circuitry 99 as above, but now with the 2 capacitors, 20 and 20' present. In another preferred embodiment the placement of capacitor 20' is used to shorten the effective length of loop 40 to a smaller loop 40" of working length L, thereby improving MRI performance by reducing stray capacitance effects and the amount of noise picked-up from the sample. In this embodiment, a section of shielded cable, such as coaxial cable 41 may be used to form the proximal portion 40' of the loop 40. By this means, stray capacitance and noise pick-up associated with the loop section 40' is substantially eliminated. This has no effect on the measurement of bio-potentials or application of RF ablation. In yet another exemplary embodiment shown in FIG. 2d, additional capacitors 20b, 20c, 20d are connected between the catheter leads 4 and 5 to further distribute the MRI tuning capacitance along the MRI-active portion of the catheter L with shielded cable portion 41 connecting this portion to circuitry 99 and 100 described above. In an embodiment, at least one tuning capacitor is provided. In this embodiment, loop 40" is tuned as before. The number of capacitors that can be added in this way is limited by the inability to tune the circuit if the capacitance becomes too large. In addition the capacitance is preferably limited such that bio-potential and/or RF ablation signals are transmitted without significant impediment between electrodes 14 and 15, and input/output connections 94 and 95.

Figure 2C:
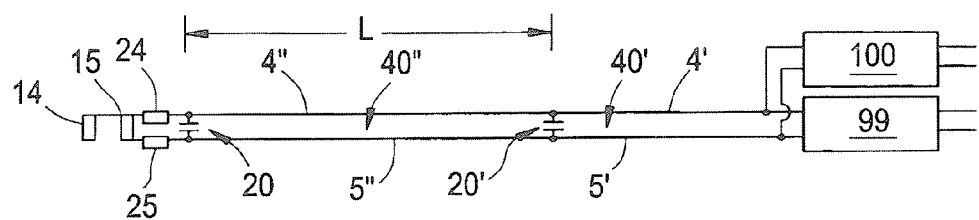
Figure 2D:
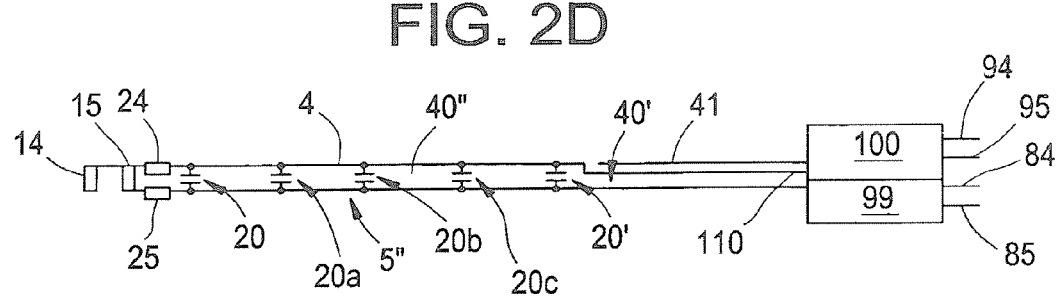

While the catheter devices that are illustrated, in FIG. 1 and FIG. 2c and FIG. 2d are depicted with two electrodes 14 and 15, this is not intended to be a limitation. Conventional catheters with different numbers of electrodes, for example with 1-7 electrodes for intra-cardiac use, are available. The multifunctional MRI probe or catheter disclosed herein can be extended to catheters with tips with different numbers of electrodes by placing the capacitor 20 immediately proximal to the plurality of electrodes, in the case of two or more electrodes. In such embodiments, the capacitor is connected across the lead 4a that goes to the proximal electrode 15a, and to any of the leads connected to a more distal electrode such as 14b, as depicted in FIG. 2c. A loop-antenna is thereby formed from leads 4a and 5a, which are connected to the circuitry 99 and 100 shown in FIG. 2b, as above. Because the other leads, e.g., leads 7, 8, can be used for measuring bio-potentials, and/or delivering RF energy for ablation thereby they may be filtered and each connected to a filter circuit 100. In addition, performance and safety are improved by providing reactances 24a, 24b, 25a, 25b etc, one for each electrode, of the same form and design as reactances 24 and 25 in FIG. 1C3, 1F, or 1G.

Figure 2E:
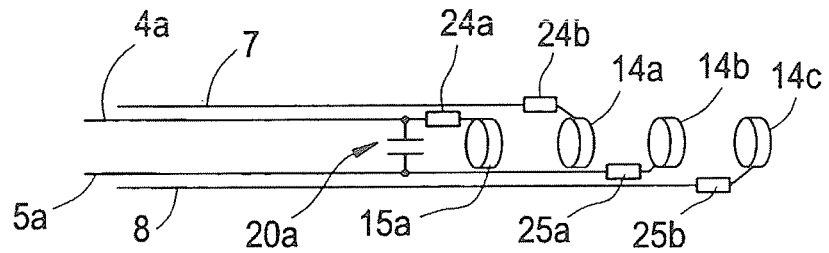
Figure 2F:
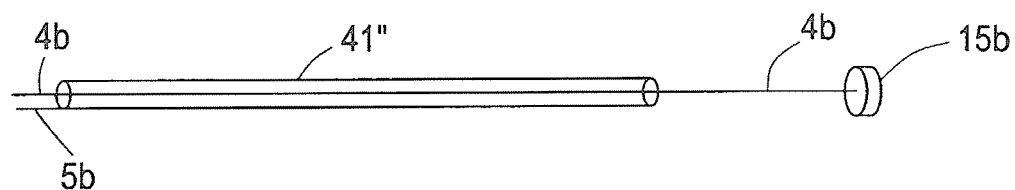

FIG. 2F depicts an embodiment in which a probe or catheter may have a single electrode, 15b. A loopless antenna, as described by and Atalar cited above, is formed by providing a shielded coaxial cable length 41" for the catheter section, with an unshielded central conductor portion extending to the single electrode 15b as shown in FIG. 2f. In this single electrode embodiment, the active or "whip" portion of the antenna extends from the electrode over the extending portion 4b, with the proximal end of 4b, and the shield of the coaxial cable fed to inputs 4 and 5 of circuits 99 and 100 shown in FIG. 2b.

In an embodiment, the electrophysiology catheter can be made to function in the mode of a loopless antenna described by Ocali and Atalar cited above, with catheters employing a plurality of electrodes. In a preferred embodiment represented by FIG. 1b, the distal end 4a of the catheter and distal electrode 14 form the MRI active end of a loopless antenna, and the connecting portions 4 and 5 form a cable portion of same. In this embodiment leads 4 and 5 are preferably formed by a shielded cable section which extends from tuning/matching/decoupling/splitting circuitry 99 and 100 to proximal electrode 15, analogous to the use of cable section 41 used in FIG. 2d described above. In particular, lead 5 is formed by the outer shielding of the coaxial cable and is terminated by the ring electrode 15. The outer shielding of the coaxial cable is insulated from the sample and is only exposed to the sample at ring electrode 15. Similarly, section 4*a* connected to electrode 14 is electrically insulated so that it is only exposed to the sample via contact electrode 14. Tuning of the loopless antenna via circuitry 99 is as described by Ocali and Atalar cited above, and the splitting circuitry remains unchanged. Note that in this embodiment reactive elements 23-26 may be omitted. In another embodiment, capacitor 20 may be omitted also.

During MRI the conducting loops formed by electrodes 14 and 15 in loopless antenna embodiments of the disclosed systems and methods, may introduce decoupling artifacts, or give rise to local heating due to currents induced in the loops by the MRI excitation field. This problem is mainly limited to distal electrode 14 because electrode 15 is attached to the cable shield. In a further embodiment these problems are minimized by electrically cutting the circular electrodes so that they cannot make continuous loops while maintaining continuous connections between the electrode and lead 4*a* and 5. This will not curtail their performance for measuring bio-potentials or RF ablation. In another embodiment, these problems are minimized by reducing the diameter of the electrodes and by forming the electrodes with a solid area of conductor covering the electrode diameter.

Loopless antenna embodiments have an advantage of shielding essentially the entire length of the catheter up to the proximal electrode, from stray capacitance and noise pick-up from the sample. In addition it provides the advantage of an MRI capability with an improved range beyond the proximal electrode 15 to the most distal portion of the catheter, the distal electrode, thereby improving image quality and resolution even closer to the target area.

Figure 2G:
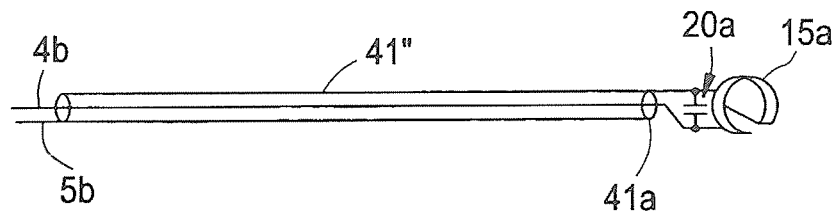
Figure 2H:
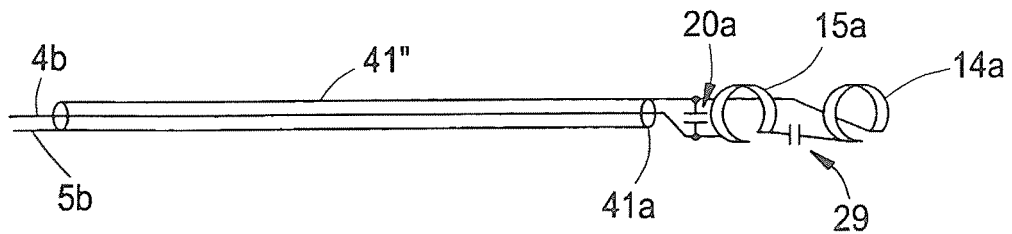
Figure 2I:
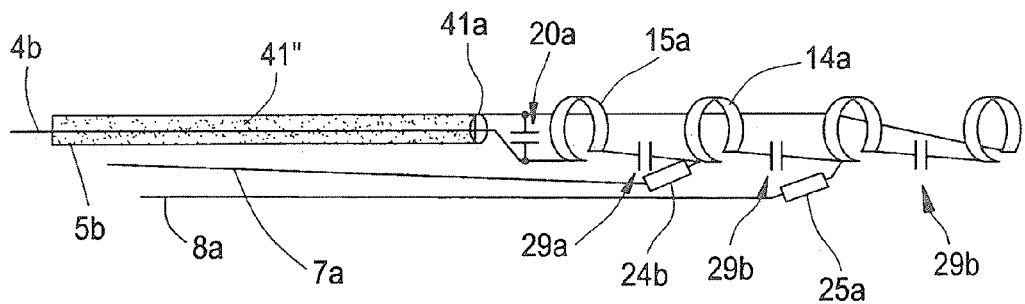
Figure 3:
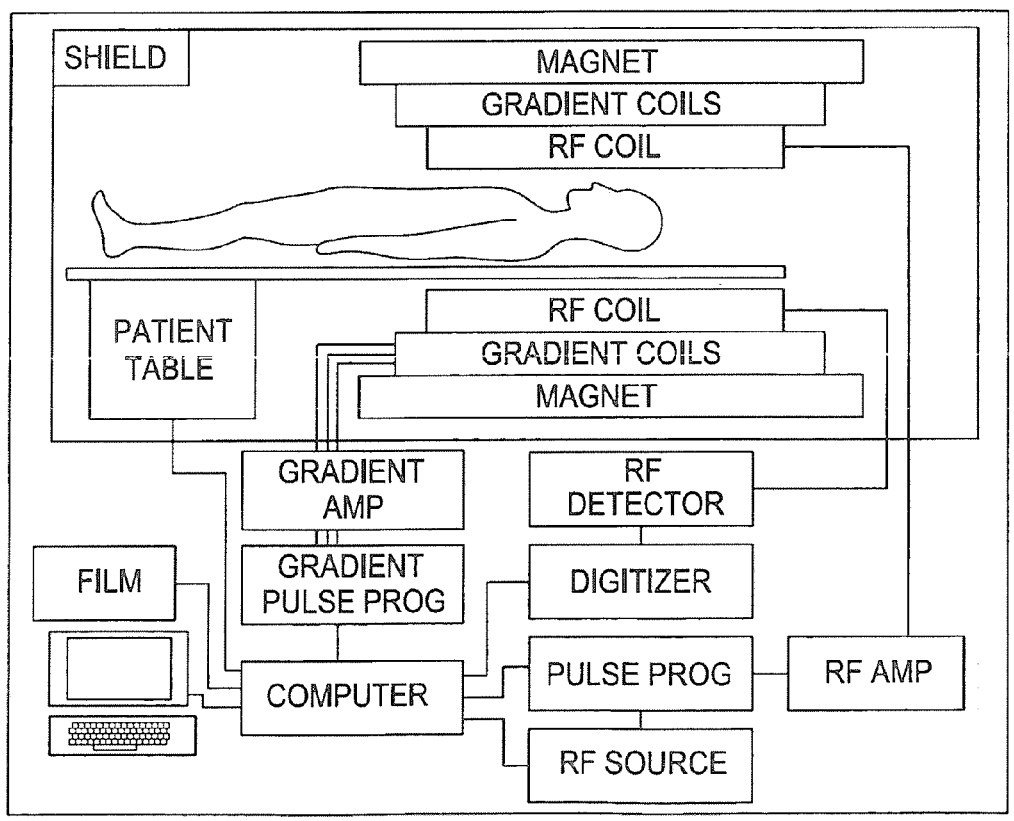

Embodiments wherein the catheter electrodes are split to form rings as described above and which share the advantages of shielding a substantial portion of the catheter length and maximizing the imaging capability at the distal end of the catheter are further described and illustrated in FIGS. 2*g*, 2*h*, and 2*i*. In these embodiments, the electrode rings themselves form loop antennas, and a portion of the catheter is formed by a section of coaxial cable 41", analogous to FIGS. 2*d* and 2*f*. A tuning capacitor 20*a* is connected across the distal end of the coaxial cable section 41*a*. In this case, the value of the capacitor is chosen, in conjunction with capacitor(s) 29(*a*, *b*, etc), such as to tune the loop formed by the distal electrode(s) to resonate at the MRI frequency. One end of each split catheter ring is connected to the next electrode via capacitors, 29, 29*a*, 29*b* etc, so that the electrodes together effectively form a helical solenoid with turns that are spaced by the separation of the electrodes. The end of the split ring of the distal electrode is connected back to the other conductor of the coaxial cable, depicted as 5*b*.

FIG. 2G depicts a single electrode loop antenna of this form for use as a multi-functional device. FIG. 2H depicts a two-electrode device. The capacitor 29 can block low frequency currents so that bio-potentials can be measured between the electrodes without being shorted out. For RF ablation, the capacitor is chosen to have a high impedance at the RF ablation frequency, winch is preferably much lower than the MRI frequency (eg, <10 MHz compared to about 64 MHz for MRI at 1.5 Tesla) to avoid interfering with MRI signals detection. FIG. 2*i* exemplifies a four electrode device. In this case, the two center electrodes are connected via additional leads 7*a*, 8*a*, which need to be connected to filter circuitry 100, as described for FIG. 2*e*. In FIGS. 2*g*, 2*h*, 2I, reactances are preferably connected on the DC lines connecting each electrode, as in 24*a*, 24*b*, 25*a*, etc in FIG. 2*e* and described above in reference to FIGS. 1C3, 1F, and 1G. While these examples are described in detail some embodiments, it will be seen that this arrangement can be extended to other numbers of electrodes on the catheters, of which it is the intent of the present application to include by reference herein.

The multi-functional catheter or probe systems and methods disclosed herein may be constructed so as to be fully MRI-compatible. Specifically, it's design and materials are selected such that (1) the image is not significantly distorted by the device; (2) the MRI electromagnetic fields do not alter the normal functioning of the device; (3) cardiac arrythmias or other nerve stimulation affects are not produced by the device, and (4) no damage to the tissue is produced by RF energy received from the MRI scanner. The presence of even small amounts of magnetic material in the imaging fields can produce substantial amounts of image distortion. This distortion is caused by perturbation of the imaging magnetic field. The most distortion is caused by ferromagnetic materials (iron, nickel, cobalt). Little if any distortion is produced by materials that do not become significantly magnetized (low magnetic susceptibility) by the MRI magnetic field. Metals which do not produce significant magnetization include copper, gold, platinum and aluminum among others. Many plastics and synthetic fibers are entirely non-magnetic and do not distort the images.

FIG. 1C shows an embodiment in which the catheter or probe is constructed based on gold-tipped, 1-15 french, most likely 7 french, MRI-compatible two-electrode ablation catheter. MRI-compatible electrode components 14 and 15, such as those used in commercial ablation catheters, or electrodes including, e.g., safe, bio-compatible, minimally corrosive materials such as gold, platinum and the like are suitable for this purpose. Leads 4 and 5 are formed from insulated conducting wire, an insulated section of flexible printed circuit board, or twin lead cable. The conductor separation should be maintained substantially constant along the length of the catheter shaft in order to promote uniform signal sensitivity and to minimize variability in tuning, which can be accomplished by twin lead cable and flexible printed circuit board, bonding an insulated wire pair together, using a twisted pair, by a multi-lumen tube to house the electrodes, by a composite tube formed with multiple lumens for the electrodes, or by separating the pair with spacers at fixed intervals with mechanisms known in the art. The conductor leads can generally be fixed to the electrodes and/or the electrical components by standard soldering or welding techniques. Ceramic chip capacitors and (non-ferrite) RF inductors wound from small diameter copper wire are preferably used for the electrical components throughout.

The shaft of the catheter is typically formed of a polymer tubing that is flexible and can be torqued within the body cavities, such as Teflon, polyolefin, polyethylene, pebax, polyurethane, or PTFE. The properties of the materials are such that the enable the device to be easily steered under MRI guidance. The diameter of the tubing should be in the range 0.8-5 mm used typically for electrophysiology procedures, or in the range 1-15 french. The total length of the catheter is in the range 0.6-2 m, but typically at least 1 m. In embodiments designed for cardiac ablation applications, the length of the invasive portion of the device is preferably at least 1.2 m long so that the tip can be placed into the heart from the femoral artery or vein, and the diameter of the device is approximately 2.5 mm. In the embodiment shown in FIG. 2*c* and FIG. 2*d*, section 41 corresponding to loop 40' can be formed from coaxial cable of diameter less than that of the shaft, and connected to circuitry 99 and 100 via standard small gauge RF-type connectors as are known and used by those skilled in the art.

In the loopless antenna embodiment corresponding to FIG. 1b wherein the entire proximal length of leads 4 and 5 up to electrode 15 are formed by a coaxial cable type configuration, similar coaxial cable of diameter less than that of the shaft, and connected to circuitry 99 and 100 via standard small gauge RF-type connectors can be used. Alternatively, the leads can be formed by flexible, torqueable insulated cable replacing the shaft altogether. In this version of the loopless antenna embodiment, the insulating shaft 10 (FIG. 1a) is replaced by the external insulation on the shaft. In yet another preferred embodiment, torqueability and maneuverability are enhanced by using coaxial cable formed by a nitinol hypotube. Similarly, the shaft that forms the coaxial cable may be constructed with an inner core that is formed from nitinol, and plated with alternating layers of gold and silver. A layer of insulation made out of FEP or PET could be used to separate the inner core from the outer conductor.

FIG. 3 shows a block diagram illustrating the operation of an MRI scanner system which may be used in connection with the disclosed systems and methods. A magnet is provided for creating the magnetic field for inducing magnetic resonance. Within the magnet are X, Y, and Z gradient coils for producing a gradient in the static magnetic field in three orthogonal directions. Within the gradient coils is an external RF excitation coil. The external RF excitation coil produces the magnetic field to excite the MRI signals in the body. A computer is provided for controlling all components in the MRI scanner. This includes the RF frequency source, spectrometer and pulse programmer. The pulse programmer generates a carefully-controlled time-sequence of shaped and/or phase or frequency-modulated RF pulses that are delivered to the RF power amplifier. The RF power amplifier has pulse power of 1-20 kW which is applied to the external RF excitation coil. The computer also controls the gradient magnetic field by providing a sequence of modulated pulses that are synchronous with the RF pulse sequence, to gradient power amplifiers, which in turn activate the X, Y, and Z gradient magnetic field coils in the magnet. Signals detected by receiver coils in response to the applied RF/gradient imaging sequences, including those detected in the aforementioned multi-functional MRI catheter system, are first input to a receiver preamplifier. These signals are amplified, phase sensitive detected, for example, by converting to digital signals and being fed to a digital receiver. The digital image data are then reconstructed in the computer and displayed as images on a monitor or the like.

It is important that the location of the tip of the catheter can be accurately determined by MRI. A number of modes of localization can be used. Because the catheter is a receiver it can be used to directly image the tissue around it. This image can be viewed on with high resolution employing a probe or catheter as disclosed herein, or, it can be viewed at low resolution as an overlay on a large field-of-view "scout" image obtained with an auxiliary coil outside the body. The location of the catheter in the body can be tracked by the bright line of signal moving in the scout image. The scout image can be updated at an interval set by the user to compensate for patient motion. An interactive control can allow the physician to "zoom in" towards the bright catheter, finally resulting in a high-resolution image in the area of the distal catheter and tip. The "zoom" function can be achieved with interactive control of the imaging gradients.

Some exemplary embodiments may include a combined multi-functional MRI catheter; a multi-functional MRI catheter connected and used in conjunction with matching/tuning/decoupling circuit means and splitting circuit means; a multi-functional MRI catheter used with said circuit means in conjunction with a bio-potential monitoring device and/or a standard RF generator for use in ablation connected at inputs 94 and 95 of FIG. 2b; and any of a combined multi-functional MRI catheter and said circuit means used in conjunction with one or more of a bio-potential monitoring device, an RF generator for ablation, and an MRI scanner. In such a system embodiment, the MRI scanner has a receiver whose inputs are connected to inputs 84 and 85.

The probe or catheter disclosed herein can be used in combination with an MRI scanner such that RF energy can be delivered to selected areas of tissue with the electrodes of the multi-functional catheter, bio-potentials measured with the electrodes, the tissue imaged with the antenna portion of the catheter. RF lesions, target tissue, catheter location and tracking may thus be visualized with the use of external detector coils or the catheter-antenna, or using external detector coils in conjunction with the catheter-antenna. This image visualization and bio-potential measurements can be used for (1) precise titration of therapy, (2) the ability to test the length and depth of lesions from new ablation-energy sources, and (3) accurate assessment of the success of making lines of ablation that block conduction.

MRI can also be used to guide other procedures. In Cardiology, accurate anatomic information, combined with electrical measurements, allows improved study of the pathophysiology of arrhythmias, stunning, remodeling, and tachycardia-induced myopathy. Outside of Cardiology, MRI-guided ablation of tumors such as metastatic liver disease, brain tumors, and prostate cancer, may allow treatment with less morbidity and less cost than conventional open surgery.

As an example of the embodiment depicted in FIG. 1c, a 100 cm long prototype catheter device for use in a 1.5 Tesla MRI system was constructed from electrode components taken from a gold-tipped, 7 french, MR-compatible two-electrode ablation catheter (Bard Inc., Murray Hill, N.J.). The two wire leads were formed from 30 gauge insulated copper wire (0.25 mm wall thickness—AlphaWire Co. Elisabeth, N.J.) with a conductor separation held constant at 1.3 mm. For the shaft of the catheter, polyolefin tubing (3.36 mm diameter with 0.5 mm wall thickness—AlphaWire Co. Elizabeth, N.J.) was used yielding a final catheter size of 10 french. A 500 pF chip capacitor (1.4×1.4×1.45 mm) was placed between the catheter leads 2 cm from the catheter tip (American Technical Ceramics Corp. Huntington Station, N.Y.). RF tip chokes 24 and 25 were not used in this implementation. This catheter was connected to circuitry shown in FIG. 2b. The catheter and circuitry are pictured in FIG. 2a.

Capacitors could have values in the range of about 1-1000 pF. Inductors could have values in the range of about 100-1000 nH. In an embodiment, the capacitor C and inductor L values can be related by the equation $L=1/(w^2C)$, where $w=2\pi B$, and where B is the resonance frequency, for example, about 64 MHz.

Figure 4:
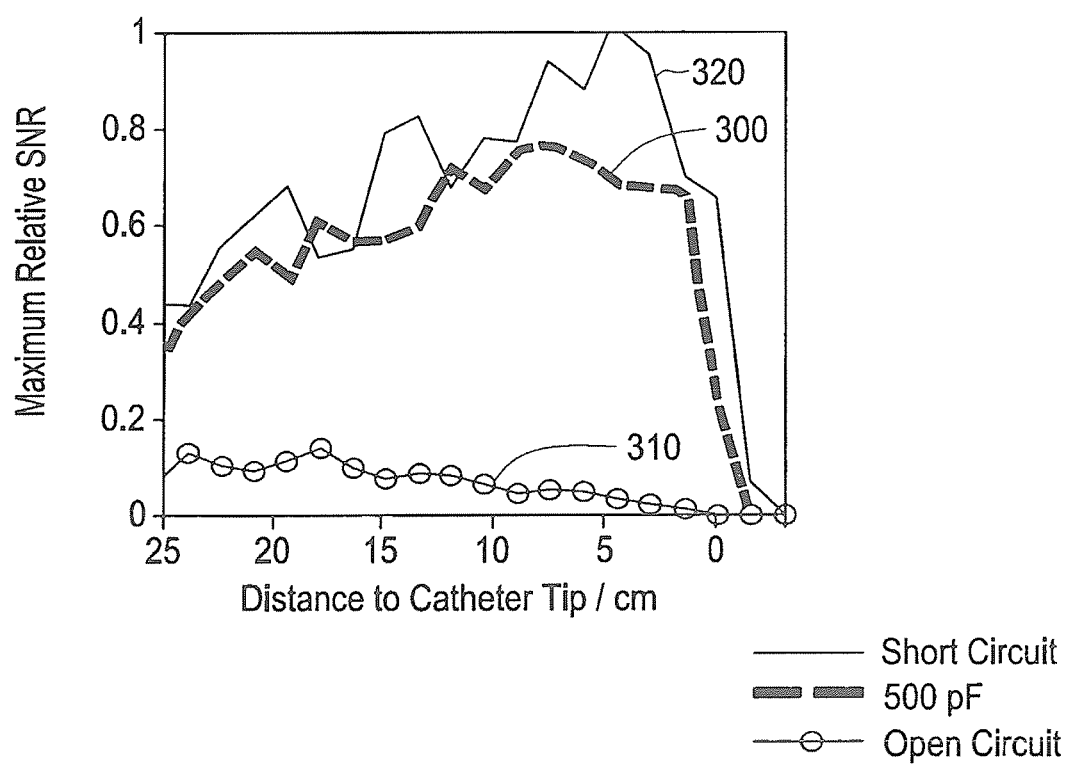
FIG. 4 shows data comparing the signal-to-noise ratio performance of some exemplary embodiments.

FIG. 4 shows the SNR performance of this example. SNR curve 300 represents that of a probe or catheter used as a standard electrophysiology catheter as in FIG. 1C. SNR curve 310 represents that of a probe with an open circuit such as in FIG. 1B. SNR curve 320 represents that of a probe in which the loop 40 is shorted, as in FIG. 1E. These data suggest that use of the example probe or catheter described above can produce a large gain in SNR compared with a standard catheter. In addition, the prototype catheter has comparable performance to the design model, FIG. 1e, which, unlike the prototype, cannot be used for electrophysiology applications.

Figure 5:
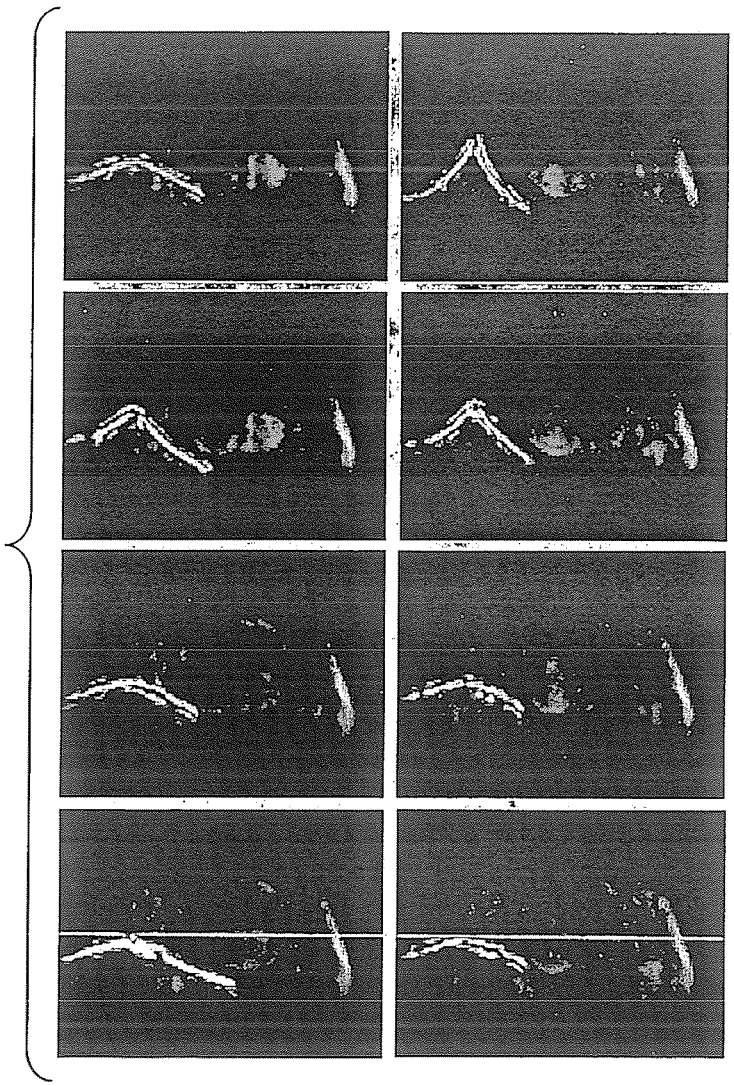
FIG. 5 shows imaging and/or tracking data according to an embodiment.

FIG. 5 exemplifies visualization and tracking of a prototype catheter. Shown are selected images from a 10-second catheter push acquired with 10 frame/sec, real-time MRI and overlaid on a static, slice-selective roadmap image obtained with a conventional external MRI coil. The location of the catheter is readily visualized by the bright line of signal. Annotations indicate the left ventricle (LV), right ventricle (RV), chest wall, and the superior vena cava (SVC). The catheter starts in the right ventricle and is then pulled up into the right atrium (Panels a & b). As the catheter is subsequently pushed, the tip stays in the atrium and the catheter body flexes (Panel c). The catheter is pulled back further (Panels d & e). In Panels f-g, the catheter is pushed once again, the tip stays in the right atrium, and the catheter shaft flexes. Note that the full length of the catheter can be easily visualized.

Figure 6:
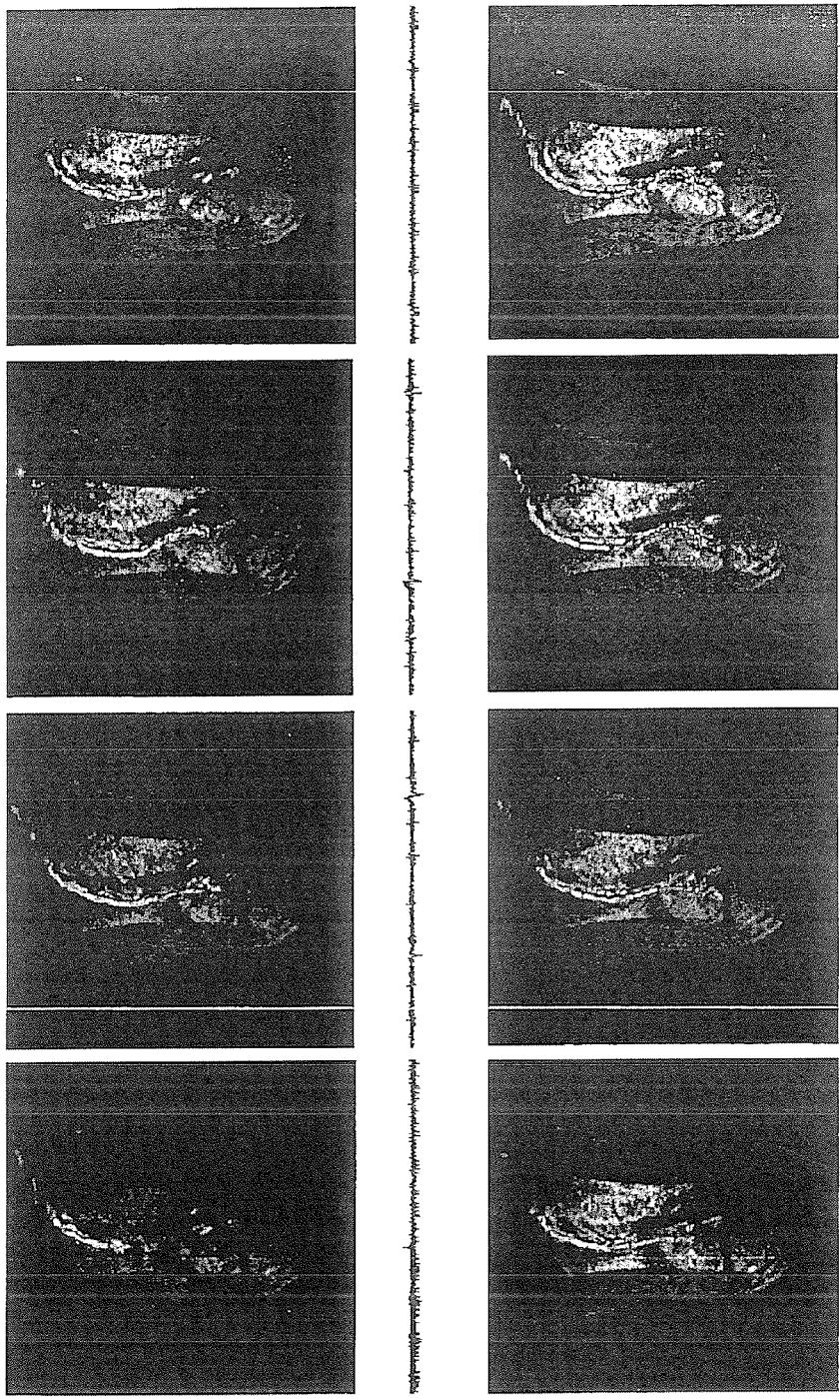
FIG. 6 shows imaging and/tracking data and biopotential data according to an embodiment.

FIG. 6 demonstrates the multifunctional operation of a prototype catheter, in the form of intracardiac electrogram recordings acquired concurrent with catheter tracking by MRI. Shown are selected images from a 15-second catheter push acquired with a 7 frame/sec, real-time MRI sequence. Annotations indicate the left ventricle (LV), right ventricle (RV), chest wall, and the superior vena cava (SVC). The catheter is initially advanced from the jugular vein down the superior vena cava toward the heart (Panels a & b). Once the catheter arrives in the right atrium, the catheter tip gets stuck and the catheter body begins to flex (Panel c). The catheter is withdrawn several centimeters, the shaft is torqued, and then advanced again (Panels d & e). As the tip is now angled anteriorly, it slips through the right atrium and into the right ventricle (Panels f & g). Note that once the catheter arrives in the ventricle, a large bipolar spike is seen in the intracardiac electrogram. Bipolar endocardial recordings typically show only electrical activation of the myocardium (in the ventricle, these spikes are concurrent with the QRS complex in the body surface ECG). In Panel h, the catheter is positioned and stable in the ventricle. Note that a strong bipolar signal is recorded once the catheter tip arrives in the right ventricle (lower amplitude signal is also seen from the right atrium).

MRI data can be used to construct 3D map or images of the areas in the heart or other organs being treated, that have undergone ablation, and the surrounding organ or tissue. Areas of ablation can typically be marked by elevated MRI transverse relaxation time values (T2), or decreased longitudinal relaxation values (T1) during infusion of an MRI contrast agent wherein contrast is enhanced by alteration of such relaxation times. A composite 3D rendering of the organ being targeted can be updated after each ablation and displayed with an appropriate rendering technique. The guidance of the catheter tip to the next site of ablation and/or bio-potential measurement, can be assisted by MRI wherein the physician uses the images to manipulate and steer the catheter, or automatic tracking and feedback could assist that physician to steer the catheter. This feature is facilitated by the current availability of MRI frame rates of 10 frames/s or more, which enables real-time catheter placement, bio-potential measurements and intervention. The lesions may be visualized using standard imaging techniques including the use of contrast agents, as discussed in U.S. patent application Ser. No. 99/25858, filed Nov. 4, 1999, entitled "System and method for Magnetic Resonance Guided Electrophysiologic and Ablation Procedures" of which this application is a Continuation On Part.

Electrical activation timing information obtained from biopotential measurements with the catheter, when combined with catheter localization information, enables accurate activation maps that are most useful in determining, for example, the site of origin of an atrial or ventricular tachycardia in the heart. Activation maps can be superimposed and/or color rendered on anatomically accurate reconstructions of cardiac structure. Spatially accurate voltage data is available from knowledge of the location of each electrode in contact with the myocardium in 3D, as derived from MRI. Thus, electrical data originating from each known electrode position allows generation of activation and voltage maps on true anatomic structures. This provides significant advantages beyond the capabilities of the non-fluoroscopic electroanatomic mapping systems that do not provide accurate anatomic information.

When the ablation/imaging catheter is used for the delivery of ablative radio-frequency energy, the high-resolution image obtained via the present catheter system enables visualization of the ablation lesion and of lesion growth. Again, directional orientation, as web as location, of the catheter lip can be determined in 3D space, and the high-resolution image data can be displayed in any plane, and in particular, in the plane orthogonal to the catheter. Since the image is obtained with the same catheter that is delivering the ablative energy, the orthogonal-plane image displays the lesion at its maximal radius, reducing the chances of underestimation as often occurs with ultrasound. High-resolution visualization of ablative lesions by the multi-functional MRI catheter or probe as disclosed herein allows for documentation of whether or not RF application resulted in successful lesion development and of where lesions have and have not yet been made. This facilitates efficient catheter placement so that RF is applied only to tissue not previously ablated.

The combination of the high-resolution visualization, biopotential measurements and/or RF ablation functionality in a single catheter as discussed above makes high-resolution MRI guidance ideal for visualization and verification of ablative lesion lines, particularly in atrial tissue. This is useful for ablation of the re-entrant circuit in typical atrial flutter and is crucial for successful ablation of atrial fibrillation. It has been shown that atrial fibrillation can be eliminated with multiple lines of ablative lesions placed in the right and left atria to emulate the surgical maze procedure. Failures of the 'percutaneous maze' procedure have resulted primarily from incomplete lesion lines. MRI guidance should allow rapid confirmation of lesion line continuity and avoidance of unnecessary repetition of RF application where tissue has already been successfully ablated.

The MRI-guided catheter bio-potential/ablation system offers advantages in ablation of ischemic and idiopathic ventricular tachycardias, ectopic atrial tachycardias, atrial flutter, and atrial fibrillation. Unlike AV node reentry and accessory pathway mediated tachycardia, these other arrhythmias have lower ablation success rates and longer ablation procedure durations, primarily due to difficulties in accurate activation mapping or confirmation of lesion development with conventional equipment. Procedure durations and risk of complications should thus be reduced substantially with the MRI-guided catheter ablation system.

While the disclosed systems and methods have been described in connection with embodiments shown and described in detail, various modifications and improvements thereon will become readily apparent to those skilled in the art. Accordingly, the spirit and scope of the present disclosure is limited only by the following claims.

That which is claimed:

1. An MRI compatible lead, comprising:
an elongated member having a proximal end and a distal end, the elongated member configured and arranged for insertion into a patient;

at least one frequency dependent circuit comprising a first conductor and a second conductor, the first conductor comprising a first inductor defined by a first coiled conductor segment and the second conductor comprising a second inductor defined by a second coiled conductor segment, wherein the at least one frequency dependent circuit comprises a first shielded parallel resonant LC circuit substantially tuned to an MRI scanner operating frequency, the first shielded parallel resonant LC circuit disposed on the first conductor at the distal end of the elongated member, the first shielded parallel resonant LC circuit comprising the first inductor and a first resonant capacitor in parallel with the first inductor; and a first electrode in electrical communication with the first conductor, wherein the first electrode is disposed at the distal end of the elongated member; and a second electrode in electrical communication with the second conductor, wherein the second electrode is disposed at the distal end of the elongated member such that the second electrode is disposed axially from the first electrode;

wherein the at least one frequency dependent circuit is configured to have a high impedance at the MRI scanner operating frequency in the MHz frequency range to thereby inhibit unwanted MRI related RF-induced tissue heating by the first electrode or the second electrode;

wherein the first coiled conductor segment and the second coiled conductor segment are both disposed at the distal end of the elongated member.

2. An MRI compatible lead according to claim 1, wherein the at least one frequency dependent circuit is also configured to allow at least one of: (a) energy in the KHz range to be delivered along at least one of the first or second conductors to at least one of the first or second electrodes, then to local tissue; and (b) at least one of the first electrode or the second electrode to detect electrophysiology signals at a low frequency and transmit the detected signals along at least one of the first conductor or the second conductor to a receiver.

3. An MRI compatible lead according to claim 1, wherein the first conductor and the second conductor comprise an insulated wire.

4. An MRI compatible lead according to claim 1, wherein the at least one frequency dependent circuit further comprises a safety capacitor extending between the first conductor and the second conductor at the distal end of the elongated member.

5. An MRI compatible lead according to claim 4, wherein the at least one frequency dependent circuit comprises a second shielded parallel resonant LC circuit substantially tuned to the MRI scanner operating frequency, the second shielded parallel resonant LC circuit disposed on a second conductor at the distal end of the elongated member, the second shielded parallel resonant LC circuit comprising the second inductor and a second resonant capacitor in parallel with the second inductor.

6. An MRI compatible lead according to claim 1, wherein at least one of the first electrode or the second electrode is configured to transmit therapeutic energy to local tissue.

7. An MRI compatible lead according to claim 1, wherein the at least one frequency dependent circuit comprises a second shielded parallel resonant LC circuit substantially tuned to the MRI scanner operating frequency, the second shielded parallel resonant LC circuit disposed on the second conductor at the distal end of the elongated member, the second shielded parallel resonant LC circuit comprising the second inductor and a second resonant capacitor in parallel with the second inductor.

8. An MRI compatible lead, comprising:
a first elongate conductor having opposing distal and proximal end portions;
a first electrode attached to the distal end portion of the first conductor; and
a frequency dependent circuit comprising an inductor and a capacitor in parallel, the frequency dependent circuit being in series with the first conductor and residing distal to the first elongate conductor, wherein the inductor and capacitor values are selected so that the frequency dependent circuit is a resonant circuit tuned to an MRI scanner operating frequency so that the frequency dependent circuit has a high impedance at the MRI scanner operating frequency in the MHz frequency range to thereby inhibit unwanted MRI related RF-induced tissue heating by the first electrode.

9. An MRI compatible lead according to claim 8, wherein the freqency dependent circuit resides proximate to the first electrode.

10. An MRI compatible lead according to claim 9, wherein the first conductor comprises an insulated wire.

11. An MRI compatible lead according to claim 10, wherein the frequency dependent circuit is configured to allow low frequency therapeutic energy to be transmitted from the first electrode.

12. A tissue ablation system comprising:
the MRI compatible lead of claim 1;
wherein at least one of the first electrode or the second electrode is configured and arranged for transmitting RF energy for ablating patient tissue.

13. The tissue ablation system of claim 12, wherein at least one of the first electrode or the second electrode is configured and arranged for transmitting RF energy for sensing electrical activity within patient tissue.

14. A biopotential measuring system comprising:
the MRI compatible lead of claim 1;
wherein at least one of the first electrode or the second electrode is configured and arranged for transmitting RF energy for sensing electrical activity within patient tissue.

* * * * *